United States Patent
Kalpin

(10) Patent No.: US 9,421,325 B2
(45) Date of Patent: Aug. 23, 2016

(54) PRESSURE BASED REFILL STATUS MONITOR FOR IMPLANTABLE PUMPS

(75) Inventor: Scott L. Kalpin, Harris, MN (US)

(73) Assignee: Medtronic, Inc., Minneapolis, MN (US)

( * ) Notice: Subject to any disclaimer, the term of this patent is extended or adjusted under 35 U.S.C. 154(b) by 484 days.

(21) Appl. No.: 12/619,145

(22) Filed: Nov. 16, 2009

(65) Prior Publication Data

US 2010/0125246 A1     May 20, 2010

Related U.S. Application Data

(60) Provisional application No. 61/116,309, filed on Nov. 20, 2008.

(51) Int. Cl.
| | | |
|---|---|---|
| *A61M 5/142* | (2006.01) | |
| *A61M 5/168* | (2006.01) | |
| *G01F 23/00* | (2006.01) | |

(52) U.S. Cl.
CPC ....... *A61M 5/14276* (2013.01); *A61M 5/16809* (2013.01); *A61M 5/1684* (2013.01); *A61M 2205/3331* (2013.01); *A61M 2205/3389* (2013.01); *A61M 2205/3396* (2013.01); *A61M 2209/045* (2013.01)

(58) Field of Classification Search
CPC ...................... A61M 5/16809; A61M 5/14276; A61M 5/1684; A61M 5/168; A61M 5/16854; A61M 5/204; A61M 2005/3114; A61M 2205/3379; A61M 2205/3396; A61M 2205/3389; A61M 2205/3331; A61M 3/022; A61M 2209/045
USPC ............................ 604/503–505; 702/55, 156
See application file for complete search history.

(56) References Cited

U.S. PATENT DOCUMENTS

| | | | | |
|---|---|---|---|---|
| 4,373,526 A | | 2/1983 | Kling | |
| 4,373,527 A | * | 2/1983 | Fischell | ............ A61M 5/14276 128/903 |
| 4,395,259 A | | 7/1983 | Prestele et al. | |
| 4,486,190 A | * | 12/1984 | Reinicke | ............ A61M 5/14276 604/67 |
| 4,784,645 A | | 11/1988 | Fischell | |
| 4,840,064 A | | 6/1989 | Fudim | |
| 4,871,351 A | * | 10/1989 | Feingold | ............ A61B 5/14532 128/DIG. 12 |

(Continued)

FOREIGN PATENT DOCUMENTS

| | | |
|---|---|---|
| EP | 0622615 | 12/1997 |
| EP | 1649884 A1 | 4/2006 |
| EP | 1839635 | 10/2007 |

OTHER PUBLICATIONS

International Search Report and Written Opinion for co-pending International PCT Application No. PCT/US2009/064693, issued Mar. 11, 2010.

*Primary Examiner* — Bhisma Mehta
*Assistant Examiner* — Jenna Zhang
(74) *Attorney, Agent, or Firm* — Mueting, Raasch & Gebhardt, P.A.

(57) ABSTRACT

The present invention includes systems and methods for detecting fluid flow into or out of a port chamber or a reservoir of an implantable medical device utilizing a pressure sensor and calculating the fluid status of the reservoir. The system detects characteristic pressure profiles associated with fluid flowing into the medical device, out of the medical device, and also whether one or both of the port chamber or reservoir are substantially empty or substantially full. In addition, the present invention may generate a sensory cue to a clinician to indicate the fluid status.

16 Claims, 21 Drawing Sheets

(56) References Cited

U.S. PATENT DOCUMENTS

| | | |
|---|---|---|
| 5,132,923 A | 7/1992 | Crawford et al. |
| 5,319,964 A | 6/1994 | Stephensen et al. |
| 5,507,737 A * | 4/1996 | Palmskog ......... A61M 5/14276 128/903 |
| 5,800,387 A * | 9/1998 | Duffy .................... A61M 5/142 604/505 |
| 5,904,666 A | 5/1999 | DeDecker et al. |
| 6,302,864 B1 | 10/2001 | Nowosielski |
| 6,315,769 B1 | 11/2001 | Peer et al. |
| 6,321,597 B1 * | 11/2001 | Demers .................. G01F 22/02 73/149 |
| 6,542,848 B1 * | 4/2003 | Neeser et al. ................. 702/156 |
| 6,740,059 B2 | 5/2004 | Flaherty |
| 6,782,339 B2 * | 8/2004 | Neeser .................. F17C 13/025 702/156 |
| 7,137,964 B2 | 11/2006 | Flaherty |
| 7,206,715 B2 | 4/2007 | Vanderveen et al. |
| 2006/0089619 A1 * | 4/2006 | Ginggen ........... A61M 5/14276 604/891.1 |
| 2006/0276744 A1 | 12/2006 | Falk |
| 2007/0106280 A1 | 5/2007 | Utard et al. |
| 2007/0239381 A1 | 10/2007 | Ginggen et al. |
| 2007/0255259 A1 | 11/2007 | Miesel |
| 2008/0243093 A1 | 10/2008 | Kalpin et al. |
| 2009/0157040 A1 * | 6/2009 | Jacobson ........... A61M 5/16804 604/505 |

* cited by examiner

PRESSURE BASED REFILL STATUS MONITOR FOR IMPLANTABLE PUMPS

RELATED APPLICATION

This application claims the benefit of the filing date of a provisional U.S. Application Ser. No. 61/116,309, filed Nov. 20, 2008.

FIELD

The present invention relates to implantable medical devices for delivering fluid to a target site within a patient. More particularly, it relates to systems, devices and methods for sensing and monitoring the withdrawal and filling of fluid into a reservoir of the medical device and estimating the fluid volume present in the reservoir.

BACKGROUND

A variety of implantable infusion devices are available for treating patients. For example, implantable infusion devices are used for delivering therapeutic substances to a target location of a patient. The implantable infusion devices are implanted subcutaneously in a convenient location in the patient. An infusion catheter is connected to an outlet of the device and positioned in the patient to allow delivery to the target location. A therapeutic substance may then be introduced percutaneously into a reservoir of the implanted device by inserting a needle into a port assembly of the device and delivering a fluid containing the therapeutic substance to the device via the needle.

Because the device is implanted within the patient and cannot be seen directly, care must be taken to monitor the withdrawal and filling of the therapeutic substance into the reservoir. For example, when removing a drug from the reservoir it is advantageous to know when the all or substantially all of the drug has been removed. Moreover, it is additionally advantageous to know when the reservoir has been filled with the new drug. Commercially available sensors that indicate the amount of fluid in the reservoir are not ideal due to size and space limitations. Such sensors may include a float connected to a variable resistor, a pressure sensor, sometimes connected to a mercury manometer, or low voltage capacitors where the fluid can go between them to register a reading.

A need therefore exists for a system capable of detecting the flow of therapeutic substance out of and into the reservoir of an implantable delivery device. A need also exists for indicating a reasonable approximation of how full the reservoir is during filling emptying and pumping procedures.

SUMMARY

The present disclosure describes, inter alia, systems, devices and methods that can be used to monitor the flow of a therapeutic substance, or other material such as a wash or rinse aid, into the reservoir of an implantable infusion device. The methods, systems and devices may be used to detect the flow into and out of the reservoir of the implantable infusion device. Moreover, the methods, systems and devices may be able to indicate a fill status, i.e., how full or empty the reservoir is, during filling and emptying procedures.

Another embodiment is a method for calculating the fill status of a reservoir in an implantable medical device, the steps including sensing a pressure differential between the reservoir and a fill port using a pressure sensor, calculating the fluid rate at which fluid is added to or removed from the reservoir based upon pressure differential and a known fluidic restriction constant for the medical device, determining the total volume of fluid added to or removed from the reservoir by integrating the fluid rate over the in which the sensed pressure change is detected, and combining the fluid volume added to or removed from the reservoir with the known starting volume of the reservoir to determine the fill status.

Another embodiment is a method for displaying a fluid status of the reservoir of an implantable medical device including calculating the fluid status by sensing a pressure differential between the reservoir and a fill port using a pressure sensor, calculating the fluid rate at which fluid is added to or removed from the reservoir based upon pressure differential and a known fluidic restriction constant for the medical device, determining the total volume of fluid added to or removed from the reservoir by integrating the fluid rate over the in which the sensed pressure change is detected, and combining the fluid volume added to or removed from the reservoir with the known starting volume of the reservoir to determine the fill status, and displaying the calculated fluid status on a programmer.

Figure 1:
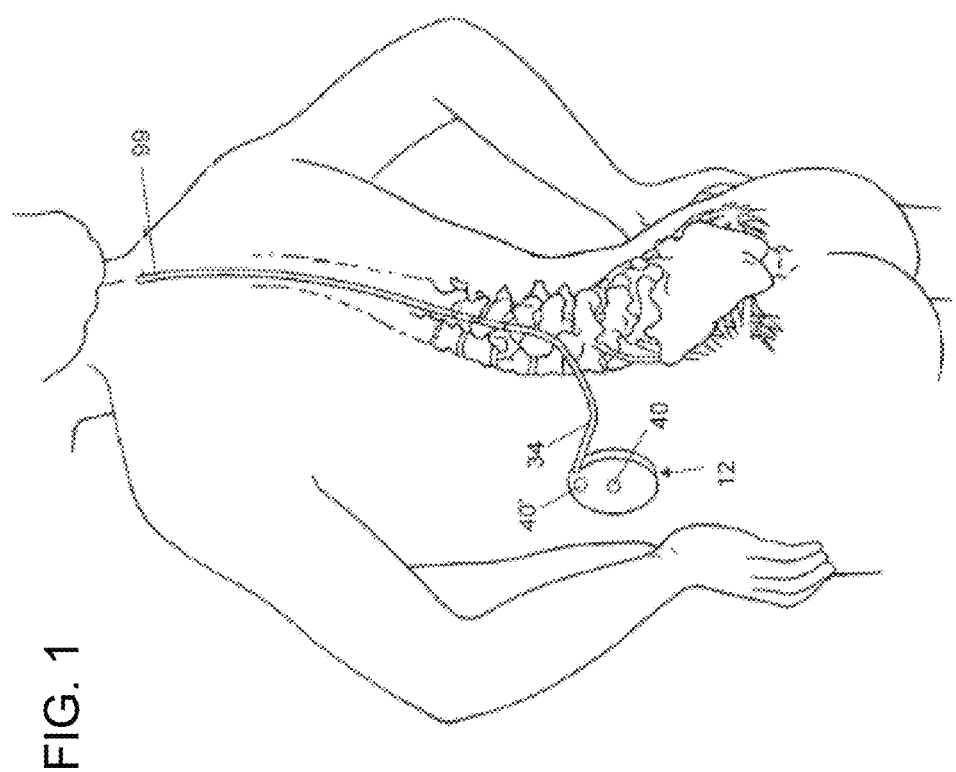
FIG. 1 is a diagrammatic representation of a perspective view of an implantable infusion system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "sensory cue" means a cue capable of being received by a person, such as an audible, tactile, or visual cue. A visual cue may include, for example, text or an image.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4.0, and 5.0) and any range within that range.

The present disclosure describes, inter alia, systems, devices and methods that can be used to detect the fluid status of a reservoir during withdrawal and/or filling of fluid into a reservoir in an implantable medical device. The systems, devices and methods can calculate a reasonable approximation of the fill status of the reservoir and report that status to a user through a display or other means. As discussed herein, it has been discovered that a decrease in pressure can be detected when the therapeutic substance, or other material such as a wash or rinse aid, (collectively "material" or "fluid"), is being withdrawn from the reservoir or has been completely withdrawn using a needle or other device that accesses a port chamber. It has also be discovered that an increase in pressure can be detected when the reservoir is being filled or when the chamber becomes fully or substantially filled. The decrease in pressure or the increase in pressure can be used to approximate a rate at which the reservoir is being emptied or filled. From that approximation a fill status can be displayed. One fill status display can be a simple gauge such as used in a car for gas or a cell phone for battery life.

Referring to FIG. 1, an implantable infusion device 12 having two port assemblies 40, 40' is shown implanted in a patient. In the present embodiment, the infusion device 12 is implanted in the side of the patient's abdomen but may, in other embodiments, be implanted in different areas of the body. In one example the infusion device may be implanted in the pectoralis area or in the buttocks. Of course, infusion device 12 may include one, two, three, or any number of port assemblies.

As shown in FIG. 1, a catheter 34 is connected to infusion device 12. Distal portion 99 of catheter 34 may include one or more openings through which fluid can flow and may be positioned at or near a target location to deliver fluid from infusion device 12 to target location. The target area depicted in FIG. 1 is the patient's spinal canal. However, it will be understood that any region of a patient's body may serve as a target area depending on the conditions, disease, or disorder to be treated. Port assemblies 40, 40' can be accessed percutaneously by a needle (not shown in FIG. 1), through which fluid may be delivered to infusion device 12.

Infusion device 12 may be any device capable of delivering fluid to a patient. For example, infusion device 12 may be an access port, e.g. a vascular access port, through which bolus injections are delivered through a catheter to a patient. Infusion device 12 may also be a device having a reservoir for holding solutions containing therapeutic substances to be delivered over a period of time. Devices that deliver therapeutic substances over time may contain fixed or variable rate pumps, programmable pumps, or the like. An infusion device 12 having a reservoir will generally include a port assembly to allow for refilling of the reservoir.

The infusion device 12 shown in FIG. 1 has two port assemblies 40 and 40', one of which may be a catheter access port 40' and one of which may be a reservoir fill port 40. One exemplary device having a catheter access port and a reservoir refill port is Medtronic's SynchroMed® II implantable infusion device (Medtronic, Inc., Minneapolis, Minn.). In addition, virtually any other currently known or future developed implantable infusion device can also be used in connection with principles described herein.

While the discussion presented herein is primarily directed to infusion devices for delivering therapeutic substances to a patient, it will be recognized that the principles described herein may be advantageously applied to a variety of devices that include fluid reservoirs.

Figure 2:
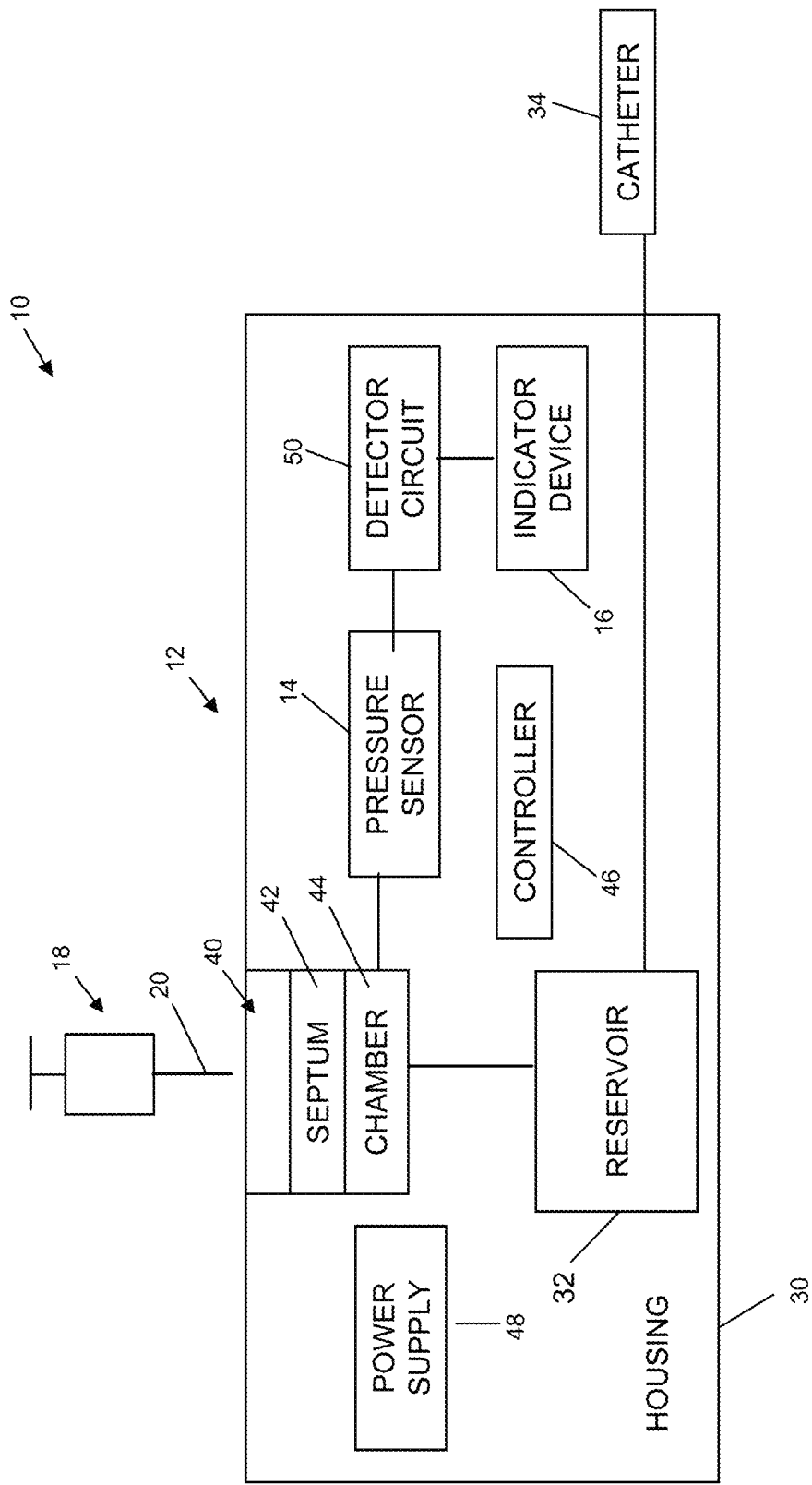
FIGS. 2-8 are block diagrams depicting implantable infusion systems or components thereof in accordance with principles of the present invention.

Referring to FIGS. 2-8, various embodiments of systems and components thereof are shown in block form. FIG. 2 refers to a representative system 10 that includes an implantable infusion device 12, a pressure sensor 14, and an indicator device 16. The indicator device 16 may be located in the infusion device 12 as shown but may also be placed in an external programmer, as further discussed below. Also depicted in FIG. 2 is a syringe assembly 18 including a needle 20 useful for percutaneously interfacing with the implantable infusion device 12. Infusion device 12 shown in FIG. 2 may include a housing 30 that maintains a reservoir 32. Reservoir 32 is designed to contain a therapeutic substance to be delivered to the patient, for example, via a catheter 34. The reservoir 32 may be a constant pressure reservoir, such as a bellows, and may be fitted with an over pressure mechanism (not shown) that disrupts and shuts off the in-flow if the pressure exceeds a pre-determined threshold.

The therapeutic substance can be any infusion agent, product, or substance intended to have a therapeutic effect such as pharmaceutical compositions, genetic materials, biologics, and others (e.g., insulin, saline solution, fluoroscopy agents, etc.). Regardless, a pump and/or metering device (or "flow regulator") (not shown) can be provided for dictating a flow of the therapeutic substance from reservoir 32 in a desired fashion. The pump/metering device can assume a variety of forms, and device 12 can further include a propellant chamber (not shown) associated with reservoir 32 for maintaining a constant desired pressure in the reservoir 32 to aid in delivering therapeutic substance to the outlet catheter 34. Other types of pumps may include piston pumps, peristaltic pumps, and others known to those in the art.

In the present embodiment, infusion device 12 may include a fill port assembly 40 fluidly connected to, and otherwise defining an inlet of, reservoir 32. In more general terms, however, fill port assembly 40 may assume a conventional configuration whereby a septum 42 seals a port chamber 44 relative to an exterior of the housing 30. Port chamber 44, in turn, is in fluid communication with reservoir 32 (e.g., a permanent fluid connection is established and a valve means is provided that actuates to selectively fluidly connect port chamber 44 and reservoir 32, etc.). Needle 20 may percutaneously deliver a liquid to port assembly 40, and in particular through septum 42 and into port chamber 44, as part of a reservoir 32 refilling operation. The therapeutic substance may then be pushed to the reservoir 32. In the present embodiment, the pressure in the reservoir 32 is less than ambient atmospheric pressure and so the needle 20 does not need to be actuated but rather the ambient atmospheric pressure initiates and sustains the flow of fluid into the reservoir 32. In further embodiments pressure may be placed on a plunger of the syringe and therefore a higher pressure may be exerted on the reservoir.

Figure 3:
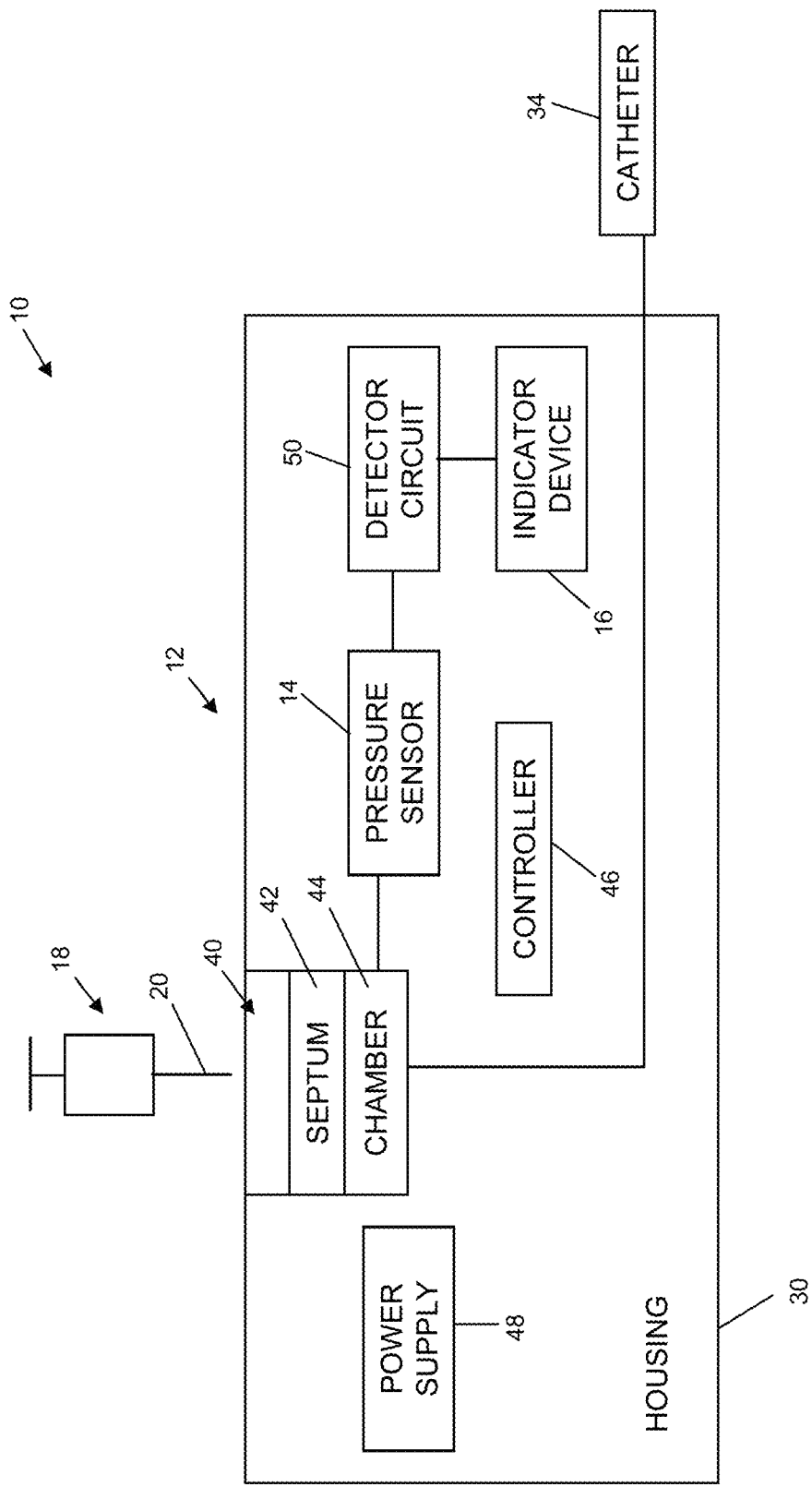

Referring to FIG. 3, an infusion device 12 without a reservoir is shown. In the embodiment shown in FIG. 3, as with the embodiment depicted in FIG. 2, port chamber 44, defined by port assembly 40, is accessible by needle 20 through septum 42. Port chamber 44 is in fluid communication with catheter 34 such that therapeutic substance infused through needle 20 into port chamber 44 will be delivered directly to a target area of a patient through catheter 34. Such a system may allow for a bolus of therapeutic substance to be directly administered.

Regardless of the embodiment depicted, infusion device 12 may include additional components as known conventionally or developed in the future. For example, infusion device 12 can include a controller 46 or other electronics, for example, in the form of a digital microprocessor, although any equivalent device may be substituted for a digital microprocessor; in many instances, it may also be desirable that the controller 46 includes data storage capabilities. Where provided, the controller 46 (as well as other components) can be powered by a power supply 48 (that may be preferably in the form of a battery or other self-contained power source). Other components can further be provided with infusion device 12 that are not otherwise illustrated, such as safety valves, flow restrictors, etc., that may enhance operation of the infusion device 12.

Figure 4:
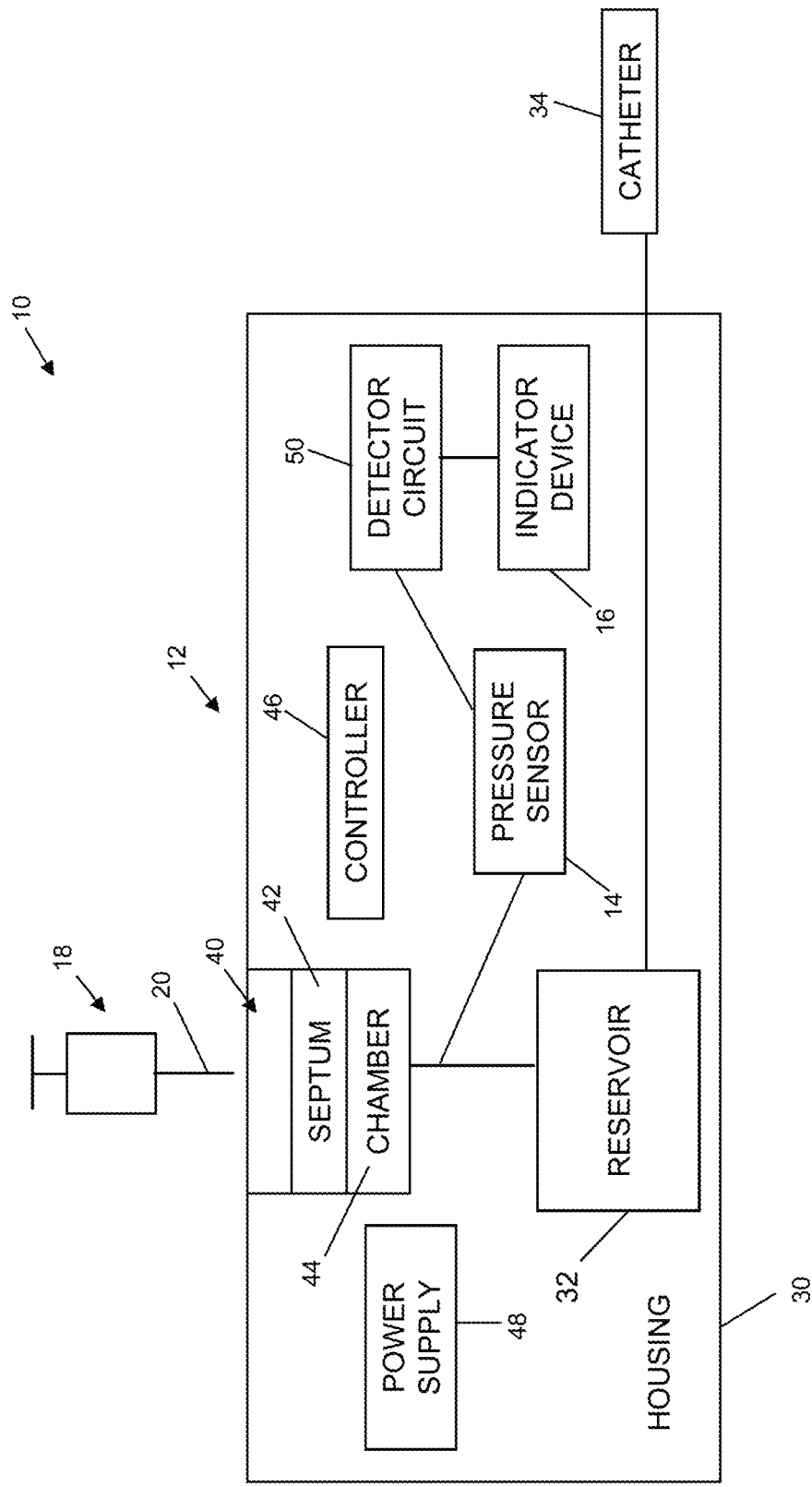

With the above general construction of the infusion device 12 in mind, a pressure sensor 14 may be maintained by housing 30, and may be operably situated between port assembly 40 and reservoir 32 (see, e.g., FIG. 4). The pressure sensor may detect pressure changes in between the chamber 44 and the reservoir 32. In further embodiments, pressure changes may be detected in reservoir 32. In various embodiments, pressure sensor 14 sends pressure-related information to a detector circuit 50 that in turn may prompt operation of an indicator device 16 (see further description below).

As depicted in the embodiments shown in FIGS. 2-4, detector circuit 50 and indicator device 16 may be included in housing 30. Detector circuit 50 may be adapted or programmed to prompt operation of indicator device 16 based upon pressure-related information generated and signaled by pressure sensor 14. For example, detector circuit 50 can be configured or programmed to prompt operation of indicator device 16 upon determining (e.g., using a logic circuit, a comparator, software etc.) that the pressure sensed by the pressure sensor 14 (or as otherwise indicated by information signaled from the pressure sensor 14) is indicative of fluid being withdrawn or added to the reservoir 32. In addition, the pressure sensed by the pressure sensor 14 may be interpreted by the detector circuit 50 as indicating the reservoir 32 is empty or full. In further embodiments, the information from the pressure sensor 14 may be further utilized to calculate the fill status of the reservoir 32. The fill status may also be known as the reservoir volume, the fill state, the reservoir level, or by other names, each indicating the volume of liquid present in the reservoir. In the embodiments shown in FIGS. 2-4, detector circuit 50 is shown as being a component apart from controller 46. In other embodiments, however, detector circuit 50 and logic circuit 50a can be provided with the controller 46 such that the controller 46 is programmed to operate indicator device 16 in a desired fashion. With regards to embodiments wherein the reservoir volume is calculated, indicator device 16 and detector circuit 50 may preferably be part of an external programmer 62 as discussed below with reference to FIG. 5.

Figure 5:
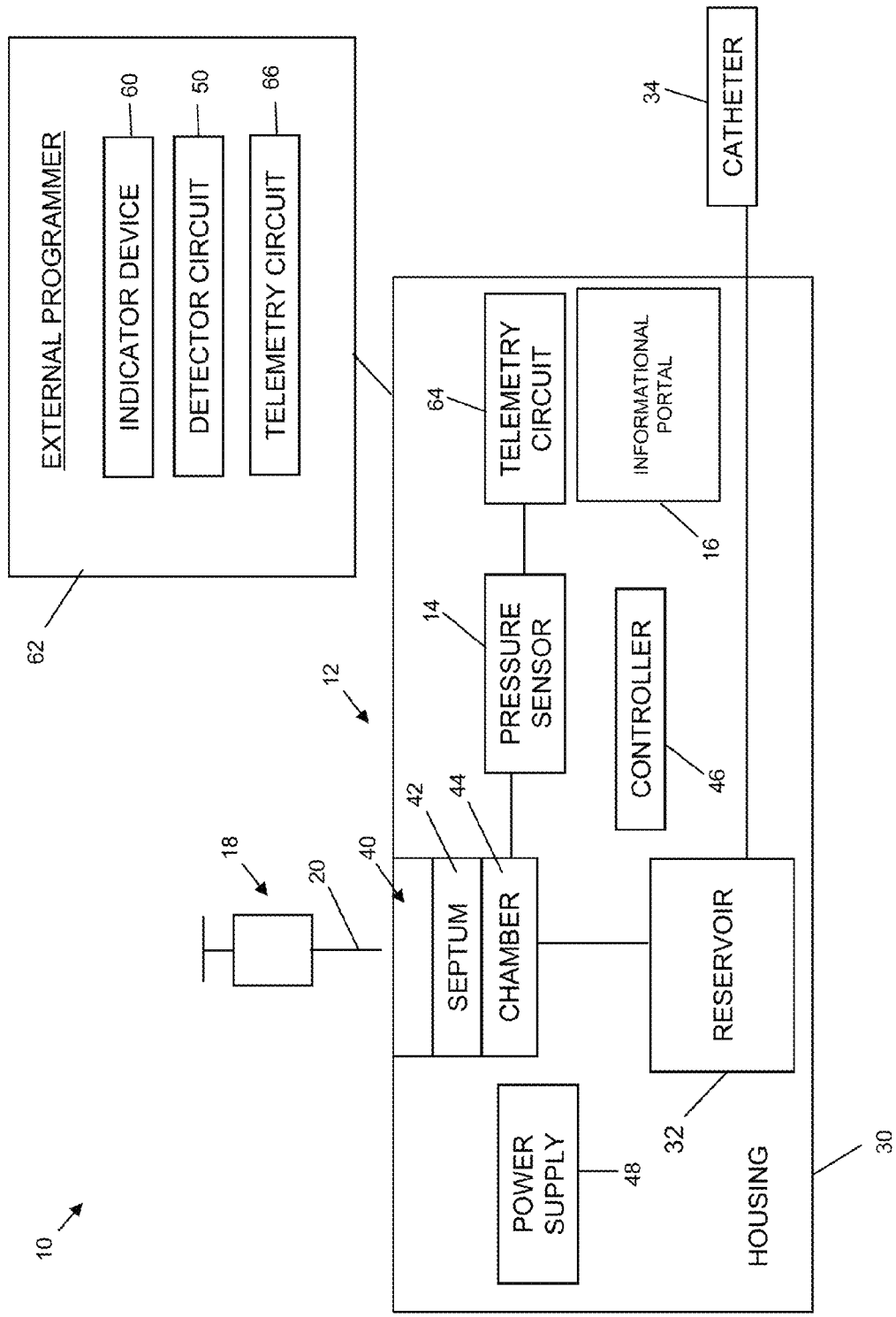

FIG. 5 is a block diagram illustrating a representative system 10 that is similar in many respects to the system 10 depicted in FIG. 2. However, with the embodiment depicted in FIG. 5, indicator device 60, detector circuit 50, and telemetry circuit 66 are located apart from housing 30, for example, as part of an external programmer 62. External programmer 62 is adapted to communicate with infusion device 12 through the patient's skin such that in various embodiments, programmer 62 and infusion device 12 are in wireless communication. Communication may be established via telemetry circuitry 64 maintained by the housing 30 and corresponding telemetry circuitry 66 maintained by the external programmer 62 (or a component (e.g., a hand-held instrument) electronically coupled to external programmer 62). Alternatively, other forms of wireless or wired communicative links between infusion device 12 and external programmer 62 can be provided.

In various embodiments, pressure sensor 14 is electronically coupled to telemetry circuitry 64 (for example, via a controller (not shown)), with pressure-related information generated by pressure sensor 14 signaled in real time or near real time to external programmer 62. External programmer 62 may run the calculations in a variety of different ways, including through software, the detector circuit 50, other hardware, firmware, or some combination, that interprets and then displays the information collected by the pressure sensor 14.

The parameters under which detector circuit 50 will prompt operation of the indicator device 60 are described in greater detail below. In one embodiment, indicator device 60 is a display screen adapted to display information to the clinician. As is known in the art, a display screen is commonly provided with an external programmer 62 (e.g., an N'Vision™ Programmer available from Medtronic as part of the SynchroMed® II Infusion System), and can display information in a variety of fashions, for example, with text, pictures, symbols, graphical information, etc. Indicator device 60 can further include a sensory cue generator, such as a sound generator. In one embodiment, upon determining that pressure-related information generated by pressure sensor 14 is indicative of some flow state of the therapeutic substance, detector circuit 50 prompts indicator device 60 to inform the clinician the fill status and flow status via the display screen, sound generating device, or the like. Screens indicating the fill status are further discussed below.

Figure 6:
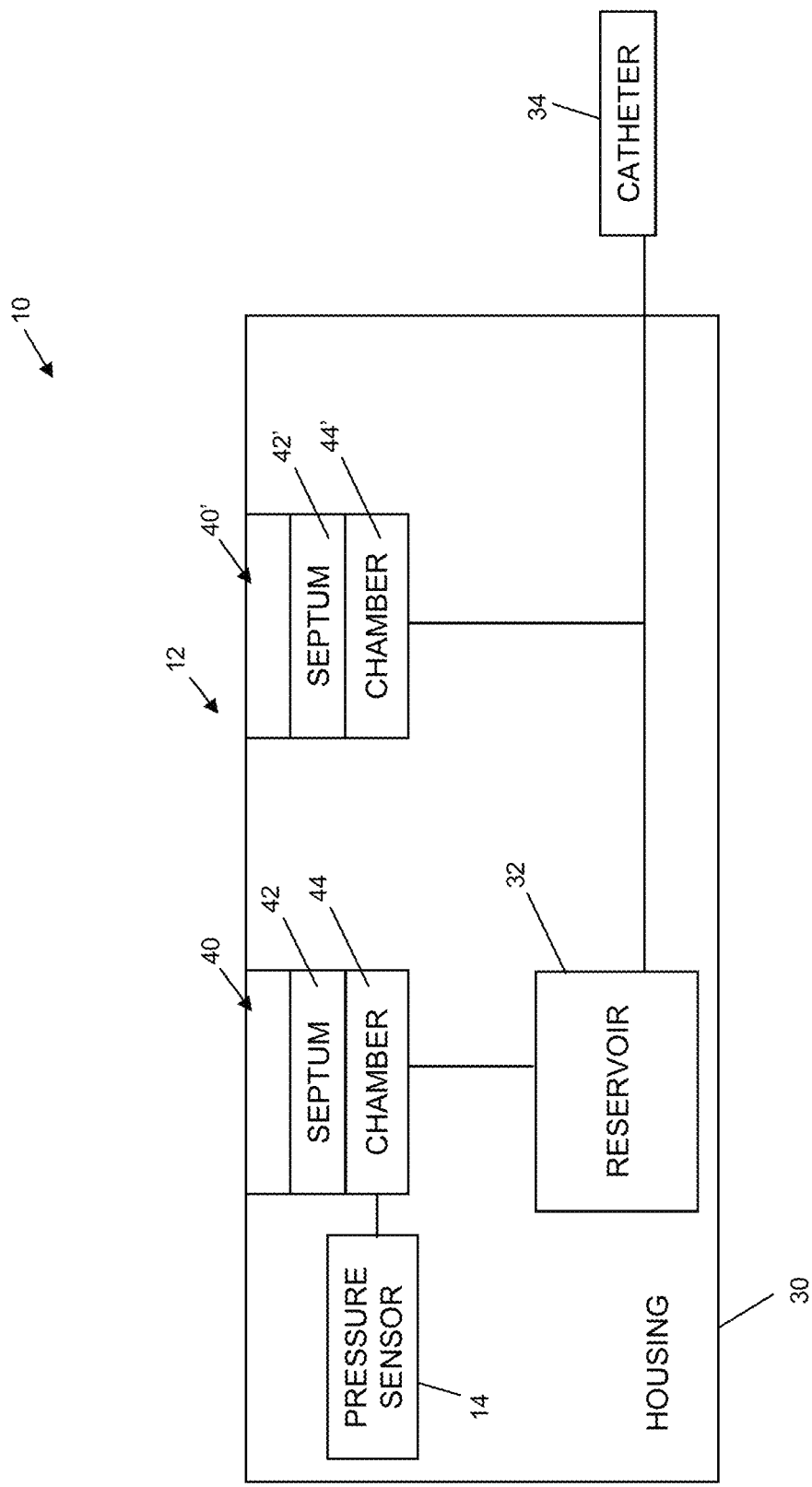
Figure 7:
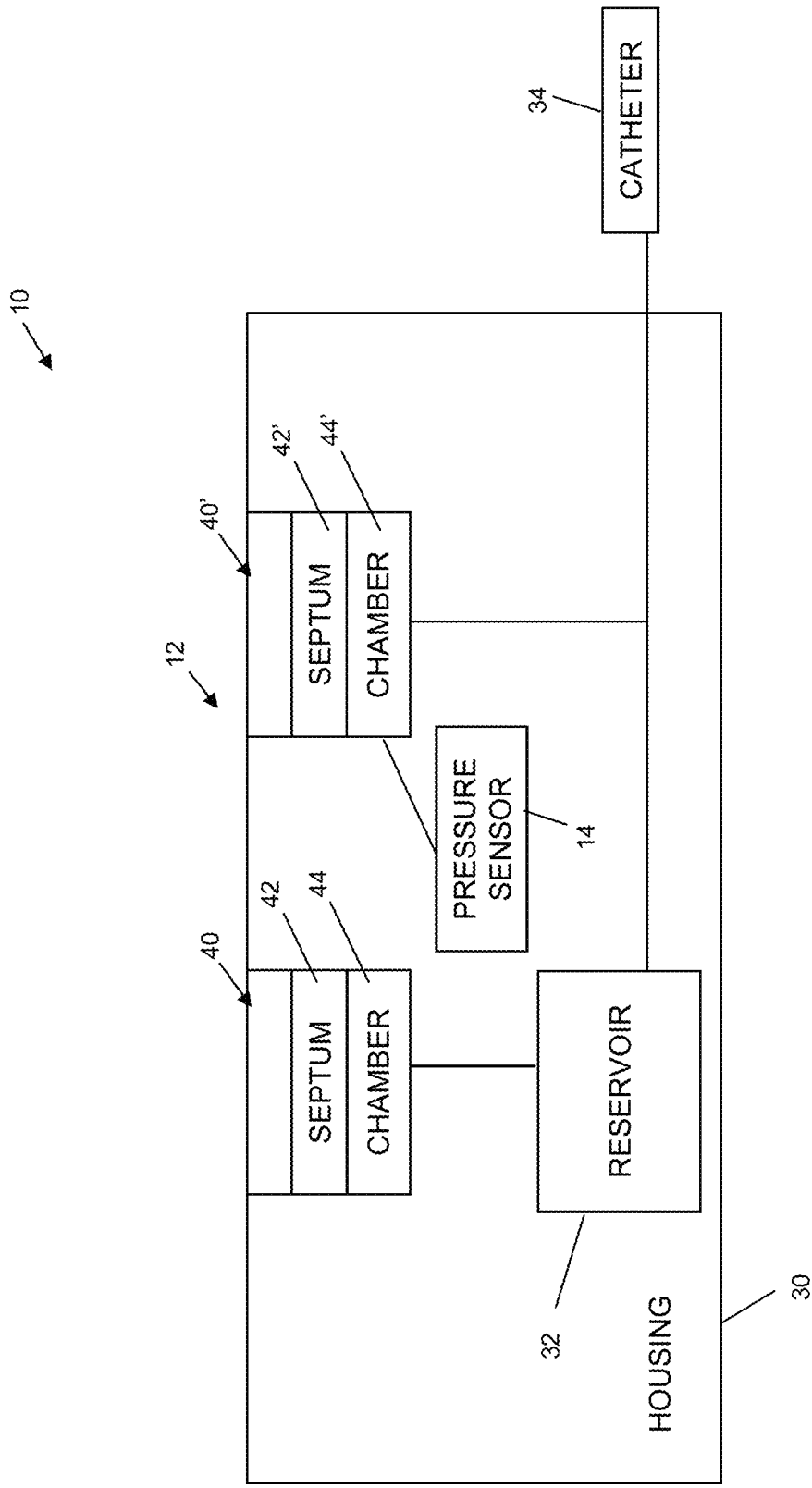
Figure 8:
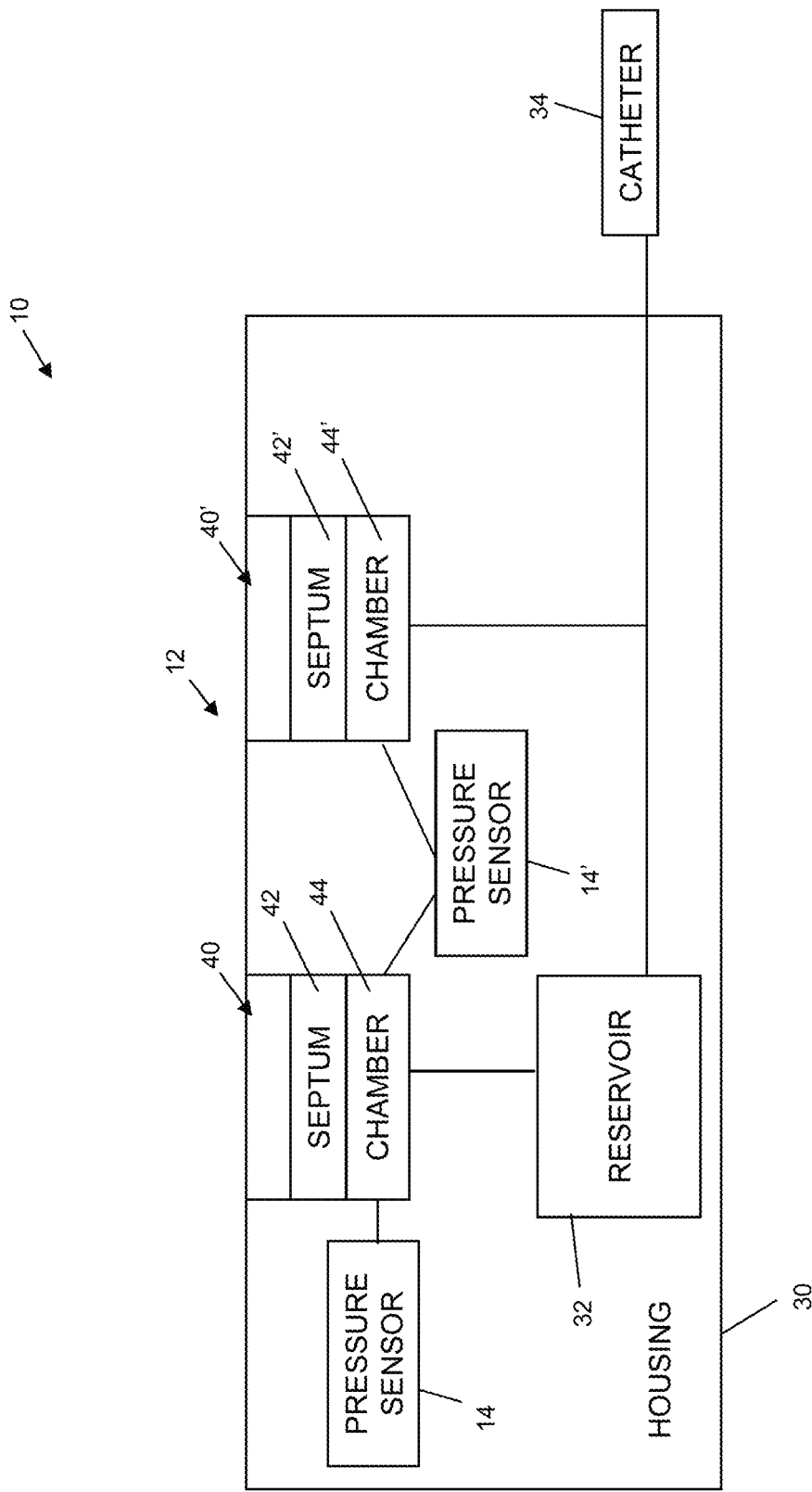

With the above description in mind, FIGS. 6-8 show alternative embodiments of system 10 in block form. While FIGS. 6-8 do not show some of the features of the devices described in FIGS. 2-5, it will be understood that one or more of the features discussed above may be included in various embodiments. System 10 as shown in FIGS. 6-8 may include two port assemblies 40, 40'. Port assembly 40 is a refill port assembly in fluid communication with reservoir 32, and port assembly 40' is a catheter access port assembly in fluid communication with catheter 34. Pressure sensor 14, 14' may be in fluid communication with fill port chamber 44 (FIG. 6), or the catheter access port chamber 44' (FIG. 7). The pressure sensor 14' may also be in direct fluid communication with the fill port chamber 44 and catheter access port chamber 44' (FIG. 8) or in communication with the passage connecting the fill port chamber 44 or catheter access port chamber 44' with the reservoir 32 or the catheter 34 (not shown). In addition, the pressure sensor 14, 14' may be in any portion of the infusion pump 12 so as to enable detection of a pressure indicative of a fluid status.

Figure 9:
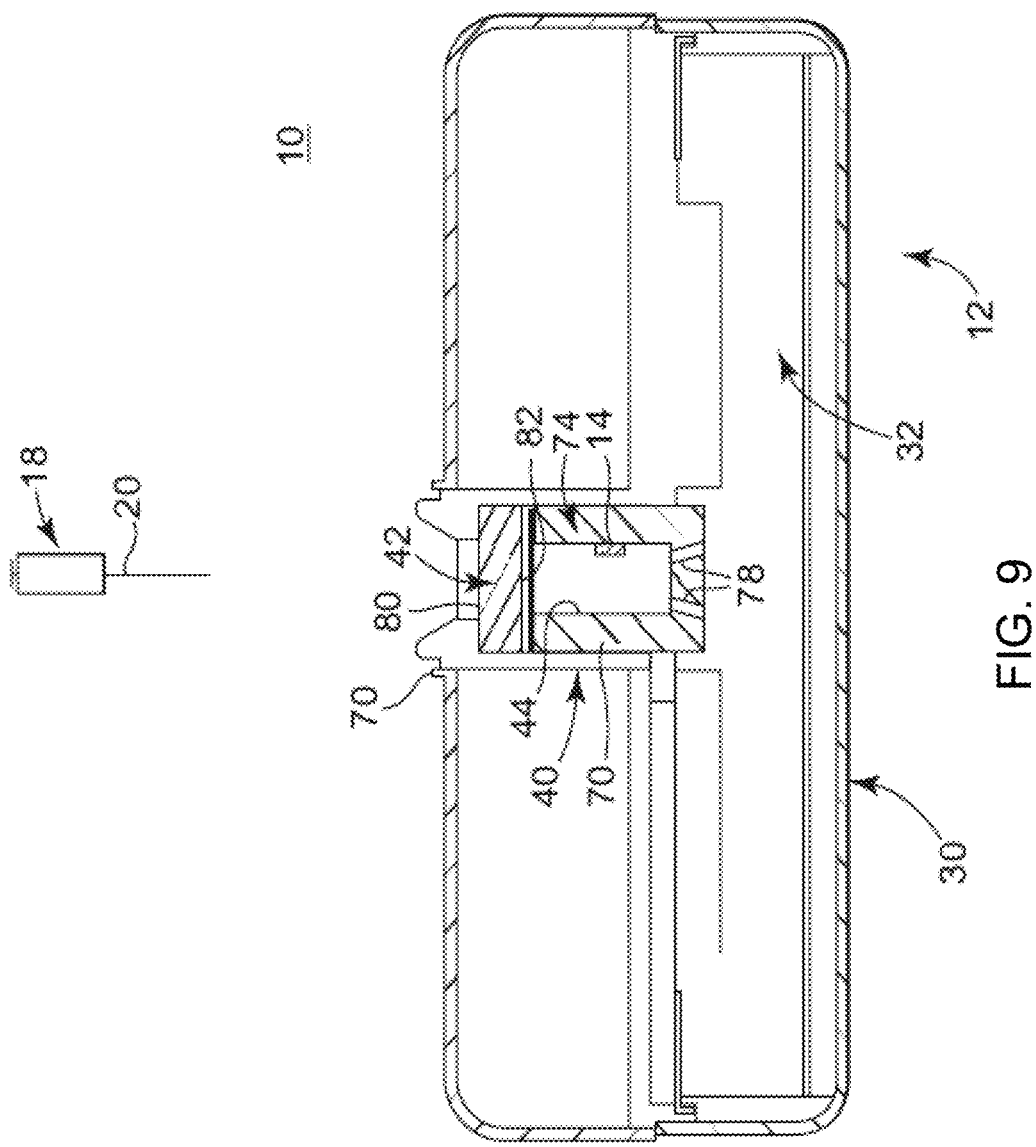
FIG. 9 is a cross-sectional view of a portion of an implantable infusion device useful with the systems of FIGS. 2-8.

FIG. 9 is a simplified, cross-sectional view of an embodiment of a portion of system 10, such as the pressure sensor 14 in conjunction with relevant portions of the infusion device 12, such as housing 30, reservoir 32, and the port assembly 40. In general terms, port assembly 40 is formed in an opening 70 of housing 30 such that port assembly 40 is exteriorly accessible relative to housing 30. Septum 42 is disposed across port chamber 44 (referenced generally) defined by a wall of port assembly 40, such that septum 42 seals the opening 70 relative to the port chamber 44/reservoir 32. Septum 42 can be manufactured of any suitable material or materials. Typically, septum 42 will be made of elastomeric materials, for example, silicone rubber, that are pierceable by needle 20 (which itself does not necessarily form a part of the system 10) and compatible with the therapeutic substance (not shown) to be contained with reservoir 32.

In various embodiments, port assembly 40 may further include a septum plug 74 used to retain septum 42 while providing a fluid-tight seal. Septum plug 74 may define the port chamber 44 to include drain holes 78 that allow fluids delivered to port chamber 44 to pass into reservoir 32. In some embodiments, a valve feature (not shown) can be provided to further control flow of liquid from port chamber 44 to reservoir 32 as is known in the art. In still further embodiments the drain holes 78 may lead to a passage (not shown) that then leads to the reservoir 32. The septum 42 may define a first exterior side 80 and a second or interior side 82. Exterior side 80 is exposed relative to opening 70 of housing 30, whereas interior side 82 defines a portion of port chamber 44. While FIG. 9 is described with regard to a fill port assembly 40, it will be understood the components described with regard to FIG. 9 can be readily applied or adapted to the catheter access port assembly.

With the above conventions in mind, pressure sensor 14 may, in various embodiments, be associated with port assembly 40, and in particular port chamber 44, by placing the pressure sensor 14 along an interior of a wall of septum plug 74. In other embodiments, pressure sensor 14 may be disposed within a thickness of septum plug 74 (such as by forming (e.g., overmolding) septum plug 74 about pressure sensor 14). Even further, pressure sensor 14 may be assembled to an exterior of septum plug 74 (relative to the port chamber 44). In further embodiments the pressure sensor 14 is placed in the drain holes 78 or in the passage that leads to the reservoir 32 from the port assembly 40.

Pressure sensor 14 may be in a variety of different forms. For example, pressure sensor 14 may be a capacitive measurement device which determines pressure by measuring the change in capacitance of a flexible membrane attached but insulated from a conductive, gas-filled cavity due to deflections caused by pressure applied over the flexible membrane. Alternatively, pressure sensor 14 may be a sensor that utilizes the piezo-electric effect or resistive change due to metallic strain in order to measure pressure applied. Regardless of the specific manner in which pressure sensor 14 measures pressure, in various embodiments, pressure sensor 14 is adapted to generate a signal indicative of a pressure of port chamber 44. Alternatively, pressure sensor 14 may be adapted to generate a signal indicative of a change in pressure of port chamber 44. Pressure sensor 14 may be any device capable of sensing and signaling information indicative of pressure characteristics associated with port chamber 44 or the passage between the port chamber 44 and the reservoir 32. Pressure sensor 14 may be electronically coupled to detector circuit 50 or indicator device 16, in a variety of ways. For example, electrical wiring (not shown) can provide the desired electrical connection. Alternatively, a wireless link may be provided between pressure sensor 14 and the processing device and/or display device selected.

In general terms and without being bound by the following description, it is believed that withdrawal or filling of therapeutic substance from the reservoir 32 causes the pressure profile existing in the fluid system to fluctuate from a normal state. In addition, when the reservoir 32 reaches an empty or full state, or a substantially empty or full state, or when the needle 20 is inserted or when clamps are opened and closed, the pressure profile may also change. Utilization of the pressure information may provide the user with reservoir fill status information and allow for a gauge to be displayed that indicates the approximate fill level of the reservoir during filling, emptying and pumping procedures, as is further discussed above.

Figure 10:
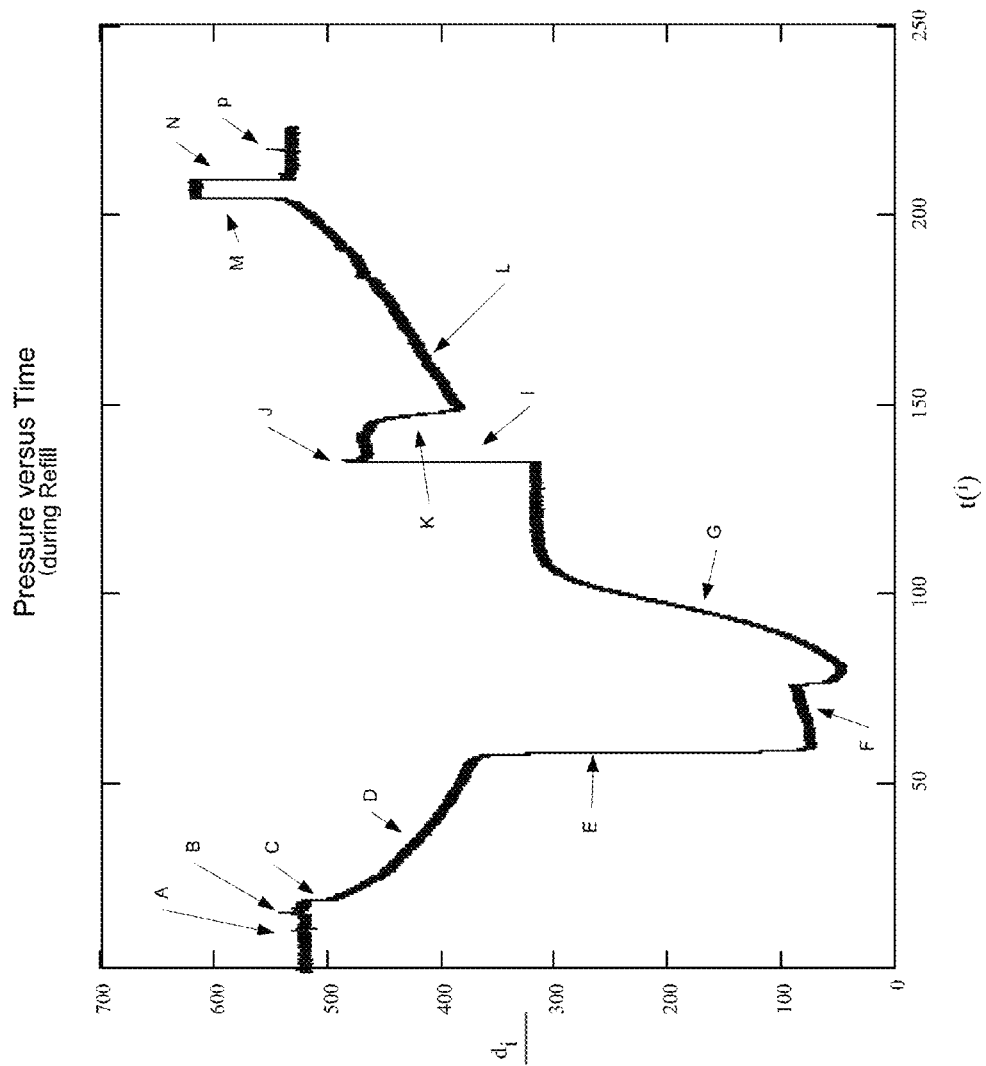
FIG. 10 is a graph of pressure over time as monitored in a reservoir of an implantable infusion device during the emptying and filling of the reservoir.

Referring to FIG. 10, an exemplary pressure profile of withdrawing fluid from the reservoir 32 and then adding fluid to the reservoir 32 will be described. Withdrawal may be undertaken when the therapeutic substance kept in the reservoir 32 is being removed. Afterward the reservoir 32 can be filled with the newly selected therapeutic substance. In some cases this may be the same therapeutic substance at a different concentration. In other cases it may be a different drug. In still further situations the reservoir 32 may first be rinsed with a different material before the new therapeutic substance is placed therein. The pressure profile shown in FIG. 10 can be obtained using any of the example systems 10 described above. Moreover, variations on the pressure profile may be obtained depending on whether a reservoir 32 is being accessed for emptying and/or filling or whether a catheter 34 is being accessed for a bolus injection. As described below, the indicated pressure may indicate a fluid flow status that is indicative of the direction of the fluid flow and how much fluid is left in the reservoir 32 or the port chamber 44.

The pressure profiles depicted in FIG. 10 were obtained by continuously sampling the pressure of the refill septum port of a prototype, bellows-based reservoir pump over the course of an entire refill procedure.

The normal pressure indicated by the pressure sensor 14 in the present embodiment infusion pump 12 is approximately 490 mmHg (about 9.5 pounds per square inch (psi)) as the present embodiment infusion pump 12 is a negative pressure pump wherein the fluid in the reservoir 32 and the port chamber 44 are kept at a pressure below normal atmospheric pressure, normally about 760 mmHg (about 14.7 psi). (The present invention, however, is just as applicable to a neutral or positive pressure reservoir pump.) FIG. 10 illustrates the reservoir 32 pressure as approximately 515 mmHg Position A on the graph shows a pressure spike when the needle 20 is inserted into the port chamber 44. In the present embodiment, the needle is connected to a tubing or hose that, during the initial insertion, is clamped off from a needle reservoir into which the fluid from the reservoir 32 will be drained or from which the fluid will be placed into the reservoir 32. Position B indicates another pressure spike when the clamp on the tubing separating the needle 20 from the needle reservoir is unclamped or released. In the presently described method the needle reservoir is empty and the fluid in the infusion pump 12 reservoir 32 will be removed before new fluid with a therapeutic substance contained therein is placed in the reservoir 32.

As illustrated at point C, when the syringe is withdrawn to create a low pressure in the needle reservoir so as to draw the fluid from the reservoir 32, a relatively rapid drop in pressure is detected by the pressure sensor 14. Fluid will begin to flow out of the reservoir 32 and the port chamber 44 at a steady rate that depends on the degree of low pressure created in the needle reservoir. Point D on the pressure graph illustrates a pressure decrease during the withdrawal (aspiration) phase of the fluid from the reservoir 32.

As may be appreciated, the steady state infusion pump 12 reservoir 32 will try to compensate and maintain the pre-programmed pressure in the reservoir 32. As the reservoir empties, the pressure will drop, but within a specific range as shown at point D. Therefore, the pressure will slowly drop as shown at point D. However, at some point the reservoir 32 will no longer be able to maintain the pressure as too little fluid will remain in the reservoir 32. When the reservoir 32 is at or near an empty state, the reservoir 32 and pressure compensation system of the infusion pump 12 may no longer be able to keep an elevated pressure, and the pressure will quickly drop as illustrated at point E. In the present embodiment the reservoir 32 may undergo the non-linear pressure behavior illustrated in FIG. 10 at point E when at or near the empty state. Point F illustrates the pressure stabilizing in the empty reservoir 32 and the port chamber 44 at some reduced pressure depending on the relative low pressure being exerted by the syringe. At point F the tubing is clamped for removal of the first syringe and connection of a refill syringe to the tubing.

Point G illustrates a relatively slow increase in the detected pressure towards the nominal pressure after the reservoir 32 is emptied and the tubing has been clamped. The increase in the detected pressure may be in part due to the inability of the pump to perfectly hold a vacuum. Micro amounts of gas may permeate through the septum.

Point I illustrates where the tubing is unclamped such that the pressure from the refill syringe containing fluid for filling the reservoir 32 is transferred to port chamber 44 and reservoir 32 and is detected by the pressure sensor 14. At point J a rapid rise in pressure is shown. In the present embodiment, the pressure in the fluid in the refill syringe is at atmospheric pressure. The pressure inside the reservoir 32 is set below this and so as the atmospheric pressure (760 mmHg) of the fluid enters the reservoir 32 the reservoir 32 tries to compensate and return to the lower selected pressure. Point K shows the reservoir 32 and propellant equalizing the pressure back to the predetermined set state. However, in the present embodiment the pressure may slowly rise such as at point L as the reservoir 32 is filled. As may be appreciated, if pressure were to be applied to a syringe plunger to increase the flow rate into the infusion pump 12, the pressure exerted may be significantly higher.

In the present embodiment, when the reservoir 32 has expanded to such a point wherein the pressure in the reservoir 32 exceeds some predetermined level, an over pressure mechanism may engage to stop the flow of fluid into the reservoir 32. Point M shows the pressure spike as the reservoir reaches a full state. Point N is the point at which the clamp on the tubing is reset. The pressure detected may then fall again as the reservoir continues to work to adjust the internal pressure to the set level. Point P shows where the needle 20 is removed and the filling operation is complete.

As can be seen from FIG. 10, during filling of the reservoir 32, an increase in pressure is observed. Again, because in the present embodiment the pump is a constant pressure pump, the reservoir 32 and propellant gases will try to compensate by reducing the pressure placed on the reservoir 32. However, there will still be a measurable increase in pressure during the time in which the reservoir 32 is being filled due to the compensation lag. As previously mentioned, the present embodiment is used with a constant pressure reservoir. One example of such a reservoir includes an accordion shaped reservoir body (which may be described as a bellows shape) surrounded by propellant gasses that keep the pressure inside the reservoir 32 constant. However, some pressure differentiation, i.e., higher or lower pressure, will occur as fluid is withdrawn as the propellant gases try to "catch up" the reservoir 32 to the pre-set reservoir 32 pressure. This may result in different pressure profiles depending on the type of system. However, still detectable pressure changes may still be indicative of fluid flow status.

Reservoir Fluid Volume

Figure 11:
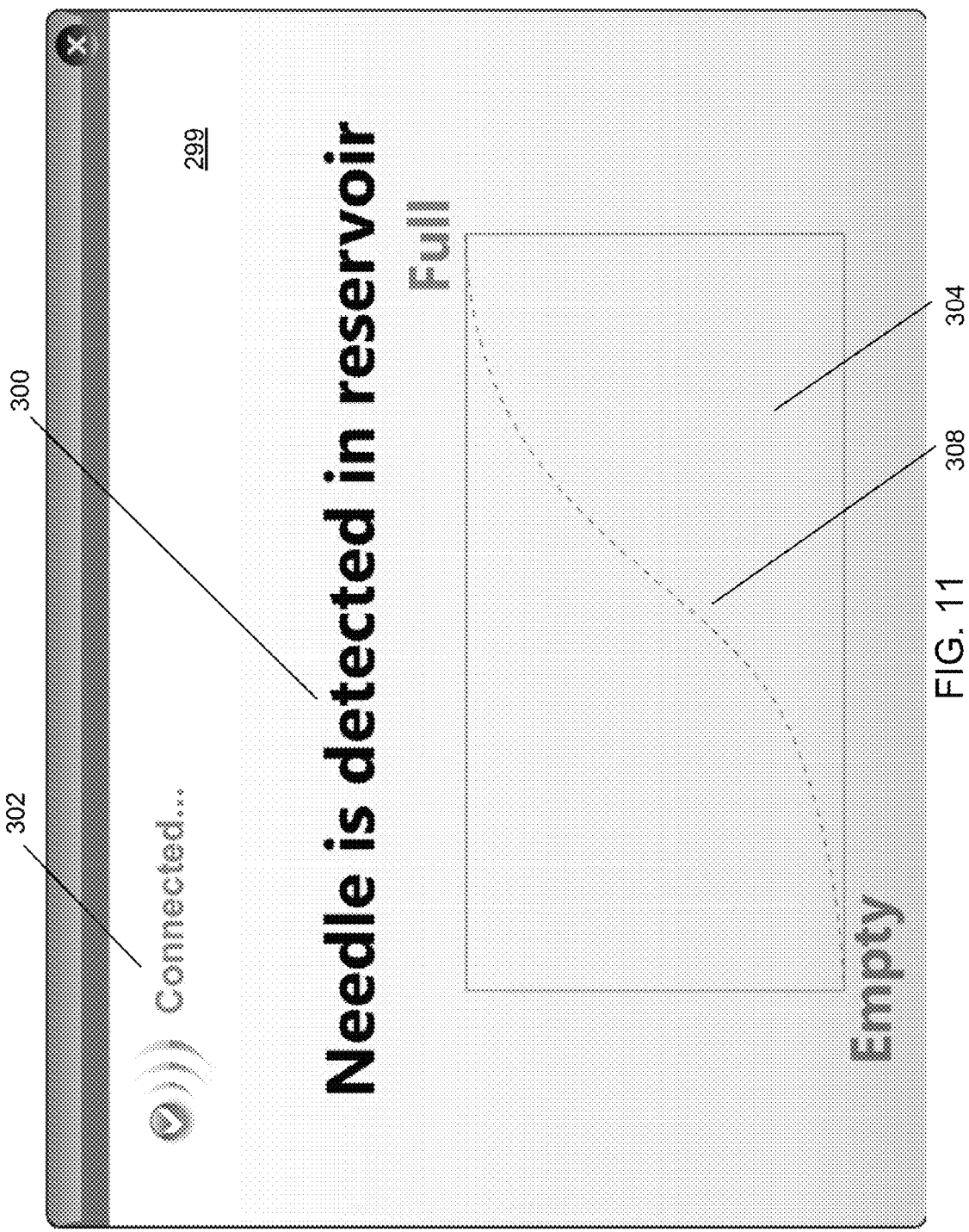
FIGS. 11-18 are illustrations of example screen shots that can be used to report the fill status of the reservoir and related information.

FIG. 11 illustrates a screen 299 for reporting information on the external programmer 62 indicator device 60 to the user. In the present screen 299 the needle 20 has been detected in the reservoir fill port 40. Screen 299 reports at 300 that the needle 20 is detected in the reservoir. (Such an indication may be actually indicative that the needle 20 has pierced the septum 42 and entered the chamber 44.) As may be appreciated, various combinations of verbiage and visual indicators can be utilized and combined to indicate the presence of the needle 20. Screen 299 further shows a gauge 304 for reporting the fill status 308 of the reservoir 32.

The fill status 308 shown on the gauge 304 will be the amount of fluid that is present in the reservoir 32. The gauge 304 may also be called an instrument, a fluid indicator, a fluid meter, or other names. At screen 299 the gauge 304 is not yet reporting the fill level of the reservoir 32. Methods of determining the fill status 308 are discussed further herein.

In this illustration, screen 299 also reports at 302 that the external programmer 62 is in communication to the infusion device 12. If the communication were to be lost, the bar may disappear or other screens may appear as further discussed below. As may be appreciated, reporting the communication connection between the programmer 62 and the infusion device 12 may be represented in a number of different ways.

Figure 12:
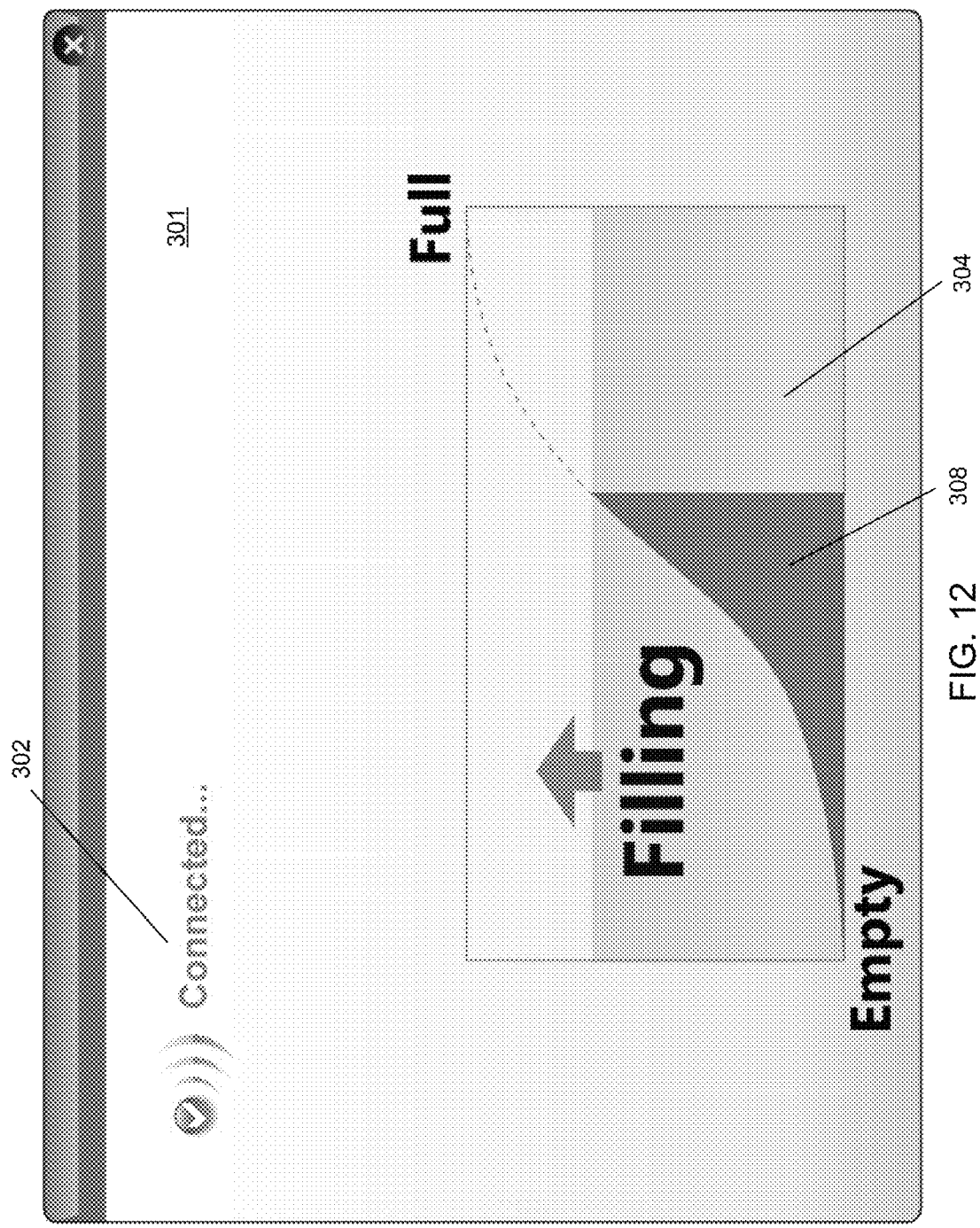

FIG. 12 illustrates screen 301 (similar to FIG. 11) wherein the gauge 304 reports a fill status 308 and a filling operation. The pressure sensor 14 has detected an increase in pressure and, when the information is transferred to the programmer 62, software in the programmer 62 interprets that information as a filling operation. In the present embodiment the screen utilizes the word "Filling" and an up arrow superimposed on gauge 304 to report that a filling operation is occurring. In alternative embodiments a variety of words and visual indicators may be mixed and matched to report this information.

Screen 301 as shown may also report the fill status 308 of the reservoir 32 on gauge 304. The fill status 308 is an indication of how much fluid is present in the reservoir 32. In the present embodiment, the fill status 308 is shown as a curve. In alternative embodiments, the fill status 308 can be shown utilizing bars, numbers, a dial, or with other graphics. The gauge 304 may or may not include units to report the fill status 308. In the present embodiment only a relative fill status 308 is displayed without units.

The fill status 308 may be based upon several pieces of information. Initially, the fill status 308 may be based on the reservoir 32 being filled after the infusion device 12 is first implanted. Programmer 62 can then start a continuous count of the amount of fluid in the reservoir 32 based on the total the reservoir 32 volume and the amount of fluid pumped from the reservoir 32. The programmer 62 can perform this and the other functions described herein using software, hardware, or some combination. Further, the calculations and other functions can be done in infusion pump 12 or in the programmer 62.

Figure 13:
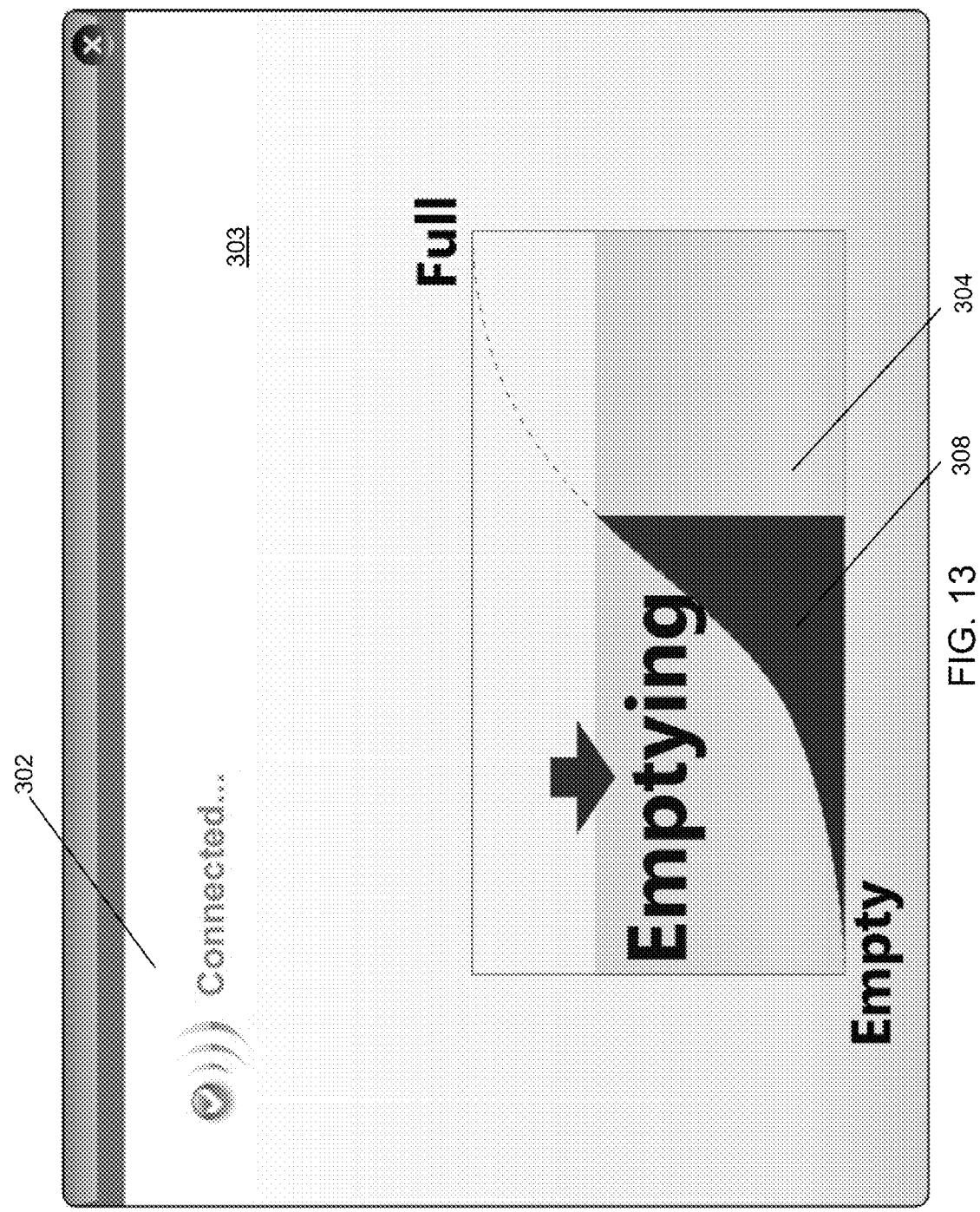

To determine the volume of fluid present in the reservoir 32, the number of pump strokes since the last reservoir 32 full state can be used to determine the amount of fluid pumped. This calculation may be based upon the known volume of fluid pumped per stroke. Alternatively, the amount of fluid pumped since the reservoir 32 was last full, based on the programmed rates and times, may also be utilized. Because the infusion device 12 has been programmed to deliver a certain amount of fluid over a certain period of time, whether in a constant dosing pattern or in a flex pattern, the fill status 308 of the infusion device 12 can be calculated with reasonable accuracy. In either case, this amount can be used to calculate the relative fill status 308 of the reservoir 32 for display on the gauge 304 when the infusion device 12 is contacted by the programmer 62 during refill or other procedures. As may be appreciated, such a calculation assumes operational connectivity between the controller 62 and implant pump 12 for the reporting of the pump stroke and reservoir 32 capacity data. The method of determining the estimated fill status 308 during filling or aspirating of the reservoir 32 is further discussed below Screen 303 shown in FIG. 13 includes the same features as previously described but reports at 306 that the reservoir 32 is being emptied of fluid. The removal of fluid from the reservoir 32 is reported by the word "Emptying" and a down arrow. As previously suggested, alternative words or symbols could be utilized to report this information. In addition, various colors may be integrated into screen 303 to help indicate the filling or emptying status.

Figure 14:
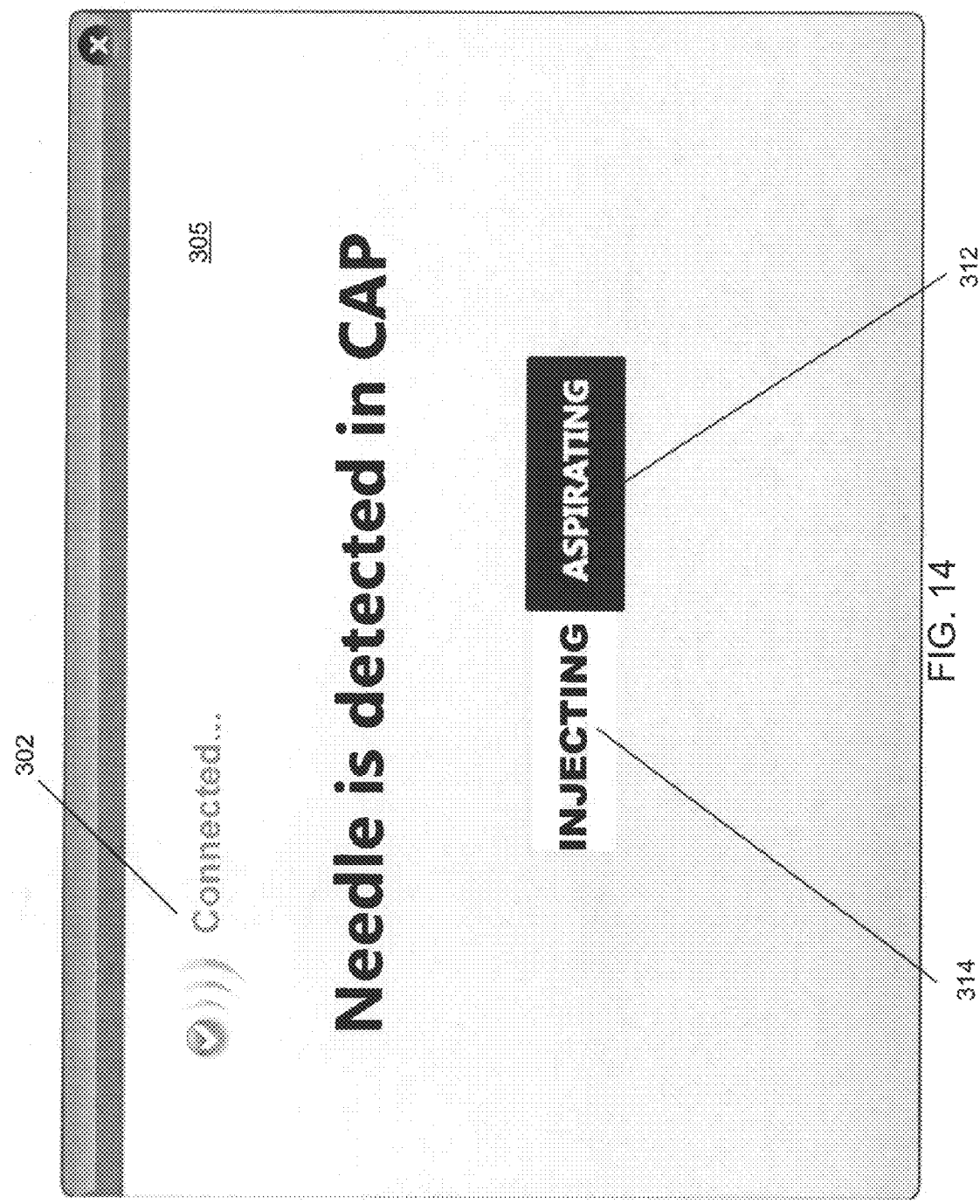

FIG. 14 illustrates screen 305 for use in providing additional information during other operations. Screen 305 indicates at 310 that the needle has been detected in the catheter access port 40' (port assembly 40'). Also illustrated is an indication that the fluid in the catheter access port 40' is being withdrawn (aspirating) at 312. Alternatively, the fluid can be reported as being injected (injecting) at 314. The fluid may be aspirated from the catheter access port 40' in order to take a sample of the fluid in which the end of the catheter is implanted, such as the cerebrospinal fluid, or to withdraw the fluid before placing another fluid therein (injecting), such as a contrast dye.

Figure 15:
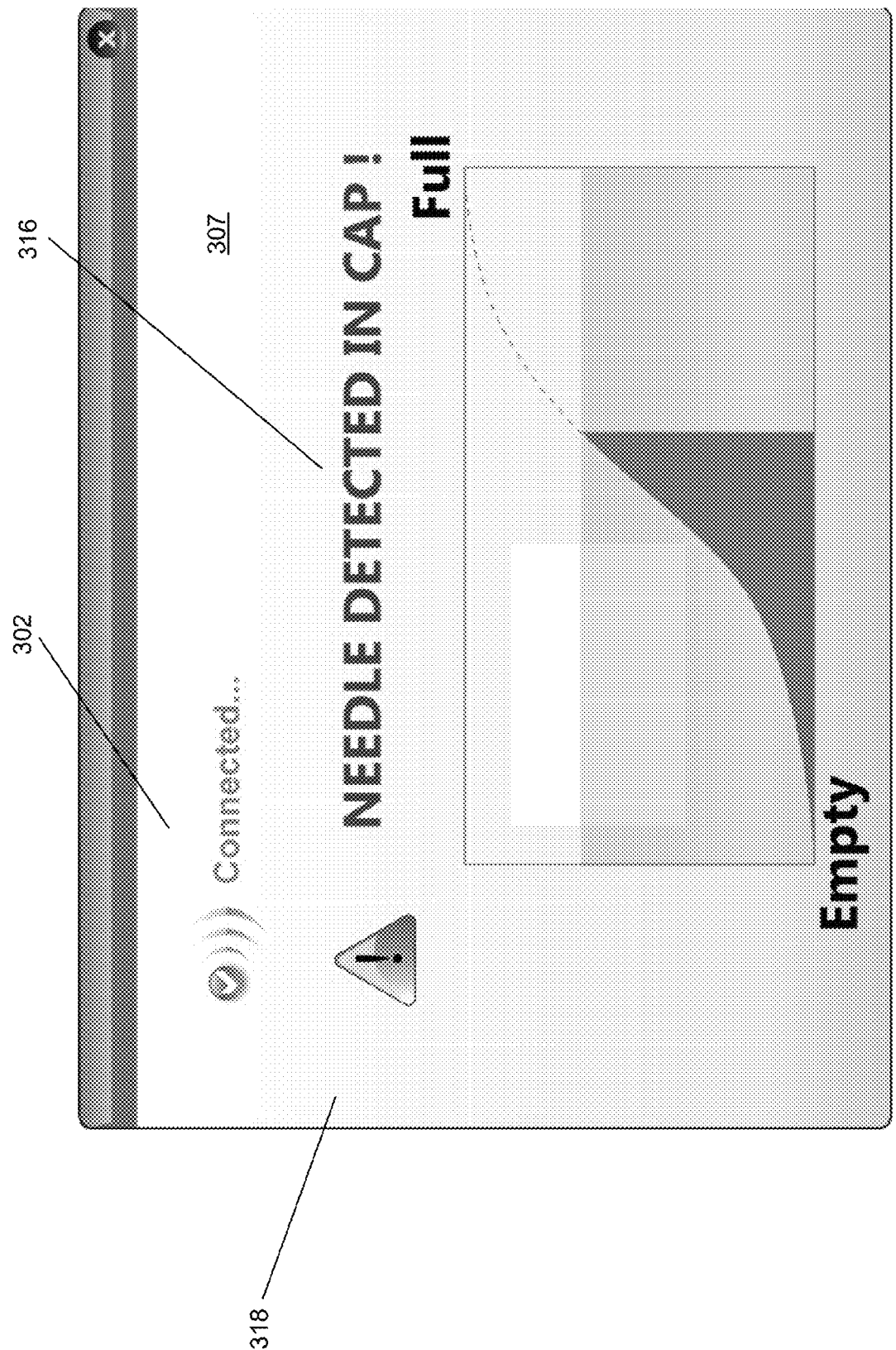
Figure 16:
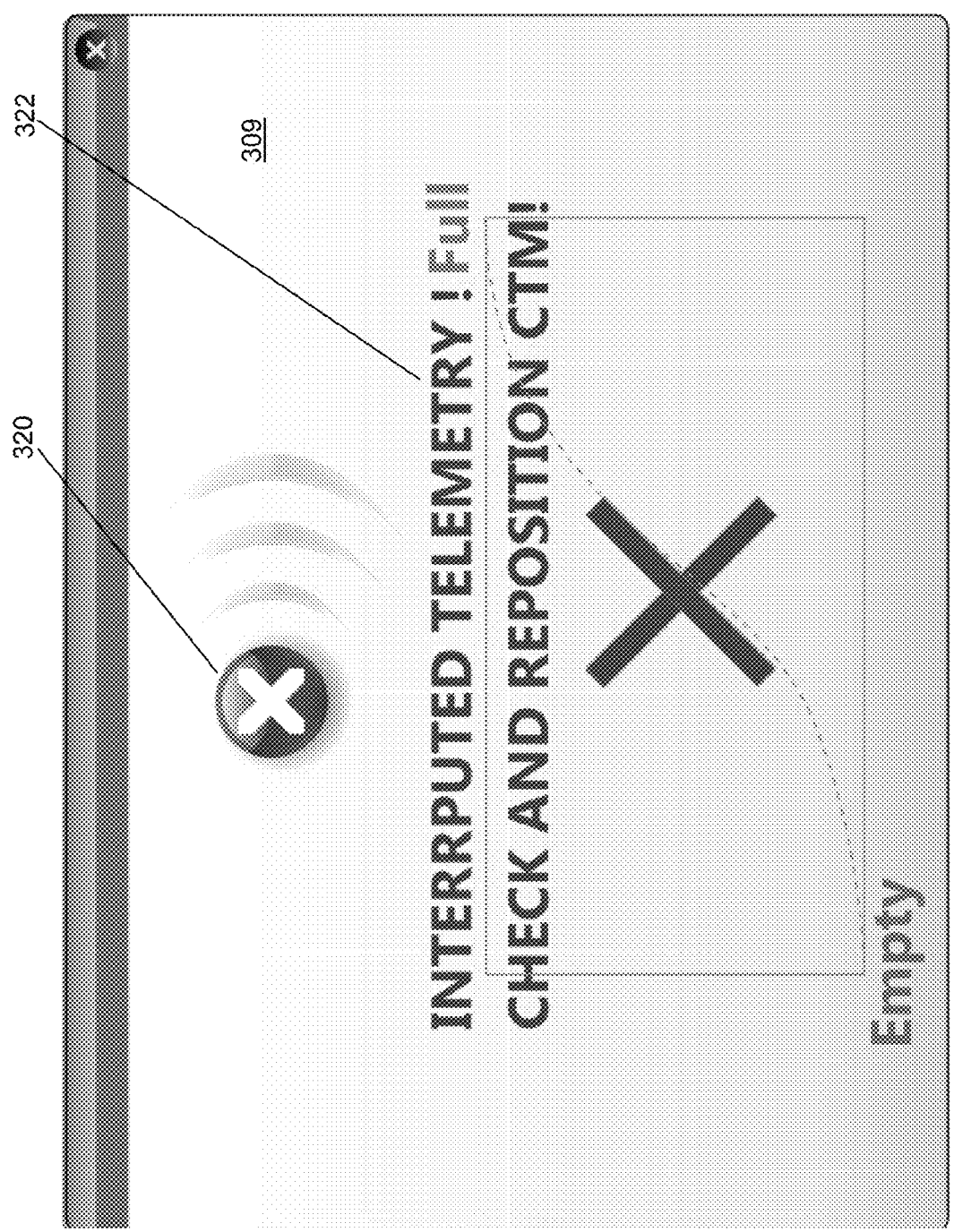
Figure 17:
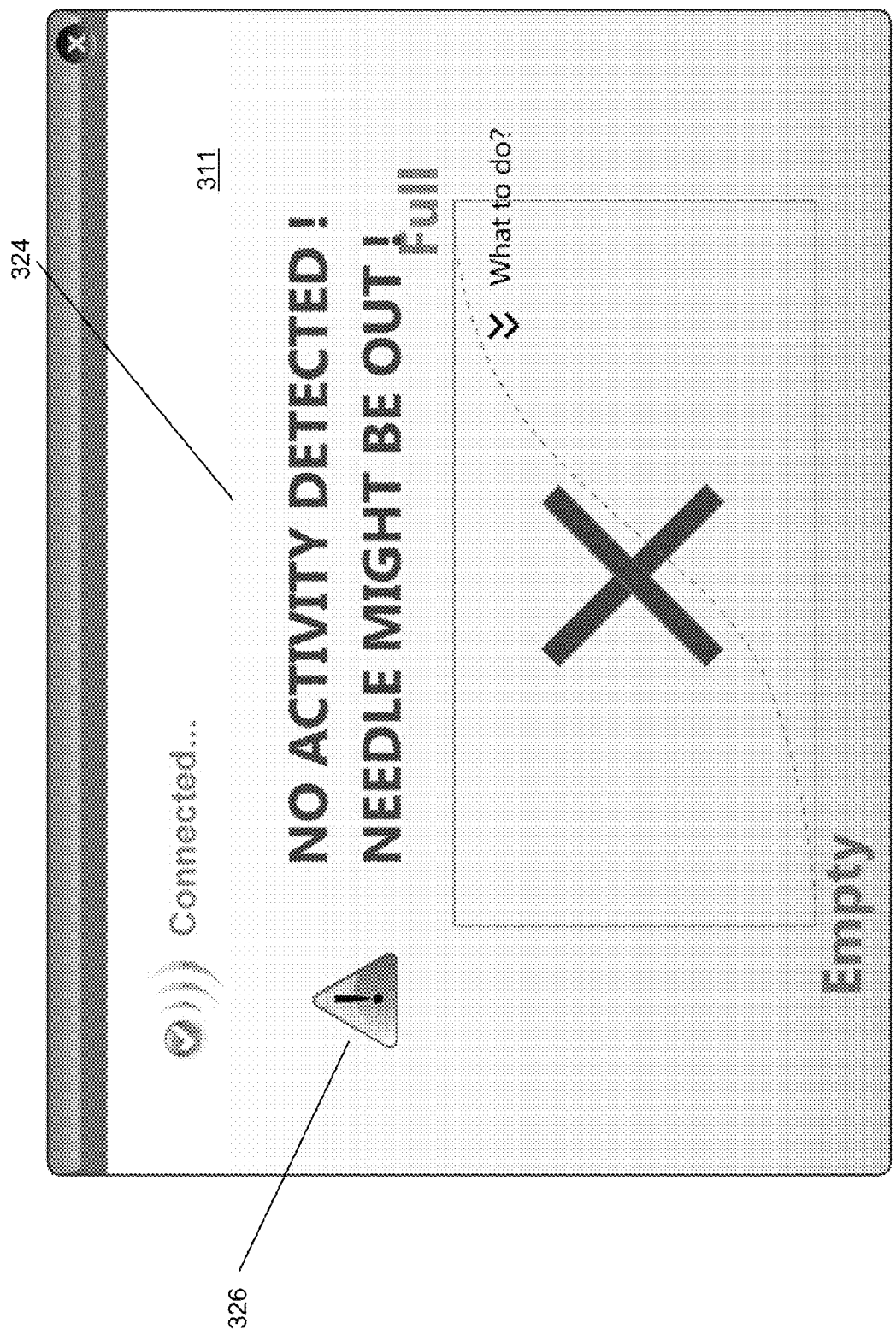
Figure 18:
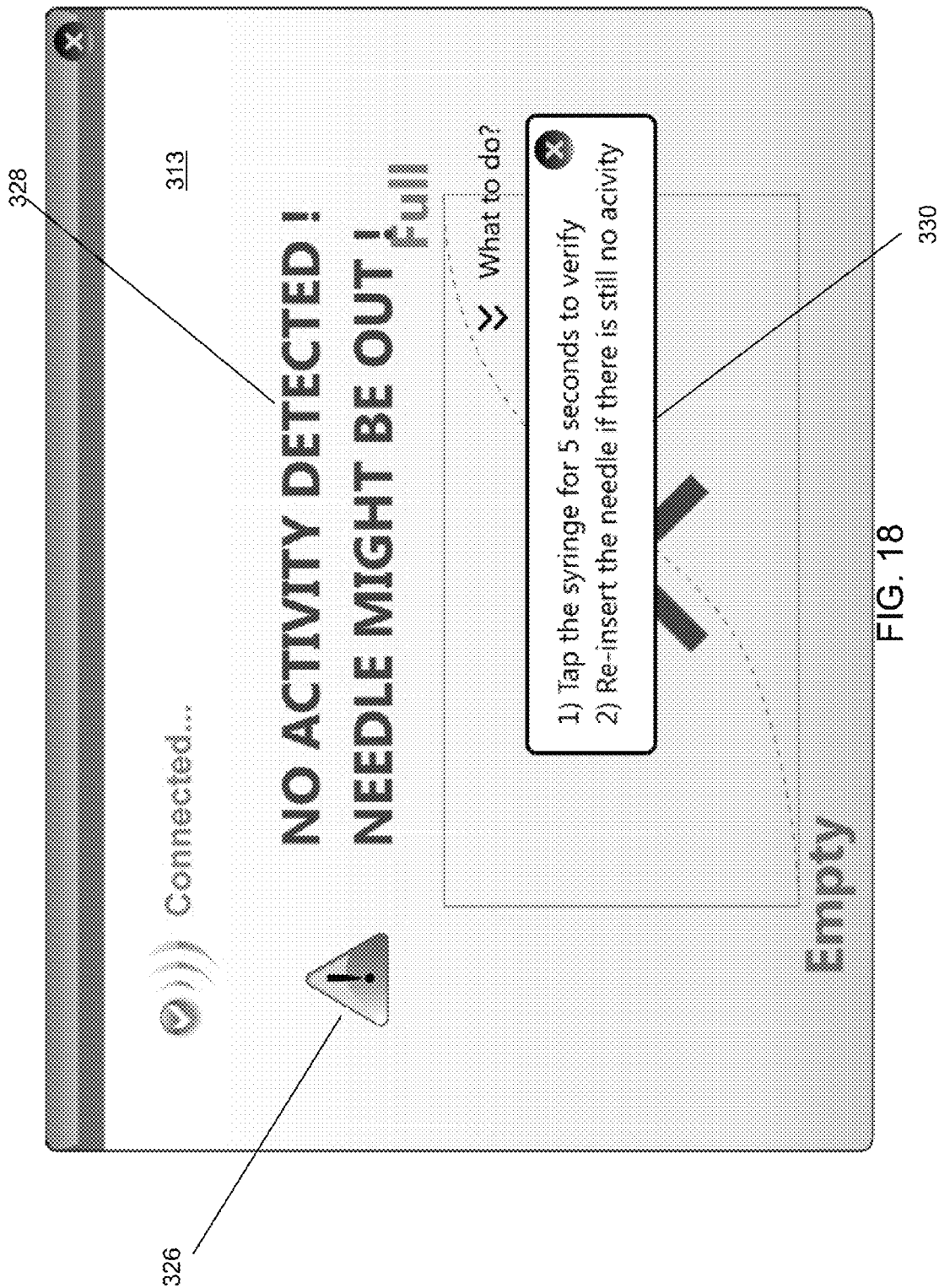

FIG. 15 illustrates screen 307 which reports at 316 that the needle is detected in the catheter access port 40'. Screen 307 may also include a warning indicator at 318. Such a warning may be utilized when the user is performing a filling operation intended to insert fluid into the refill port assembly 40 and not the catheter access port 40'. The warning may indicate to the user that the syringe 20 has been placed through the wrong septum FIGS. 16-18 are representative screens 309, 311, and 313, respectively, that show further warnings that may be given in various situations depending on the information detected by the pressure sensor 14 and the interpretation by the software of that information. Screen 309 illustrates when the communication between the infusion device 12 and the external programmer 62, illustrated previously at 302, has been interrupted. Such a warning may be displayed at 320 with an illustration and at 322 with words.

Screen 311 may indicate at 324 that no activity has been detected for a set period of time. Screen 311 may be utilized after the needle 20 has been detected in either port assembly 40, 40'. Pressure sensor 14 should normally detect when the needle 20 is moved or used during a filling or emptying operation. If no further activity is detected for a set period of time during filling or emptying the system indicates that no activity has been detected. Screen 311 will help to indicate to the user that the needle 20 has not been moving. If the user has not been moving the needle 20, the warning can simply be cleared. In other situations, the failure to detect movement might be indicative of another problem, such as dislodgement of the needle from the septum. A symbol as illustrated at 326 may be an additional indicator.

Screen 313 illustrates a notice at 330 to tap the needle to verify that the needle is still properly placed in the port assembly 40, 40'. Tapping the needle 20 will provide a pressure variation that should be detected by pressure sensor 14 to indicate that the needle 20 is still properly placed.

Volume Calculation

The total volume of fluid in the reservoir 32, or fill status 308, may be calculated for reporting on gauge 304. In one method, the calculation will rely on the reservoir 32 starting in a full or empty state. Such a state may exist after the infusion device 12 is first implanted (empty) or first filled (full). For example, if the reservoir 32 is empty, the calculations can be undertaken based upon a zero volume fluid state.

Figure 19:
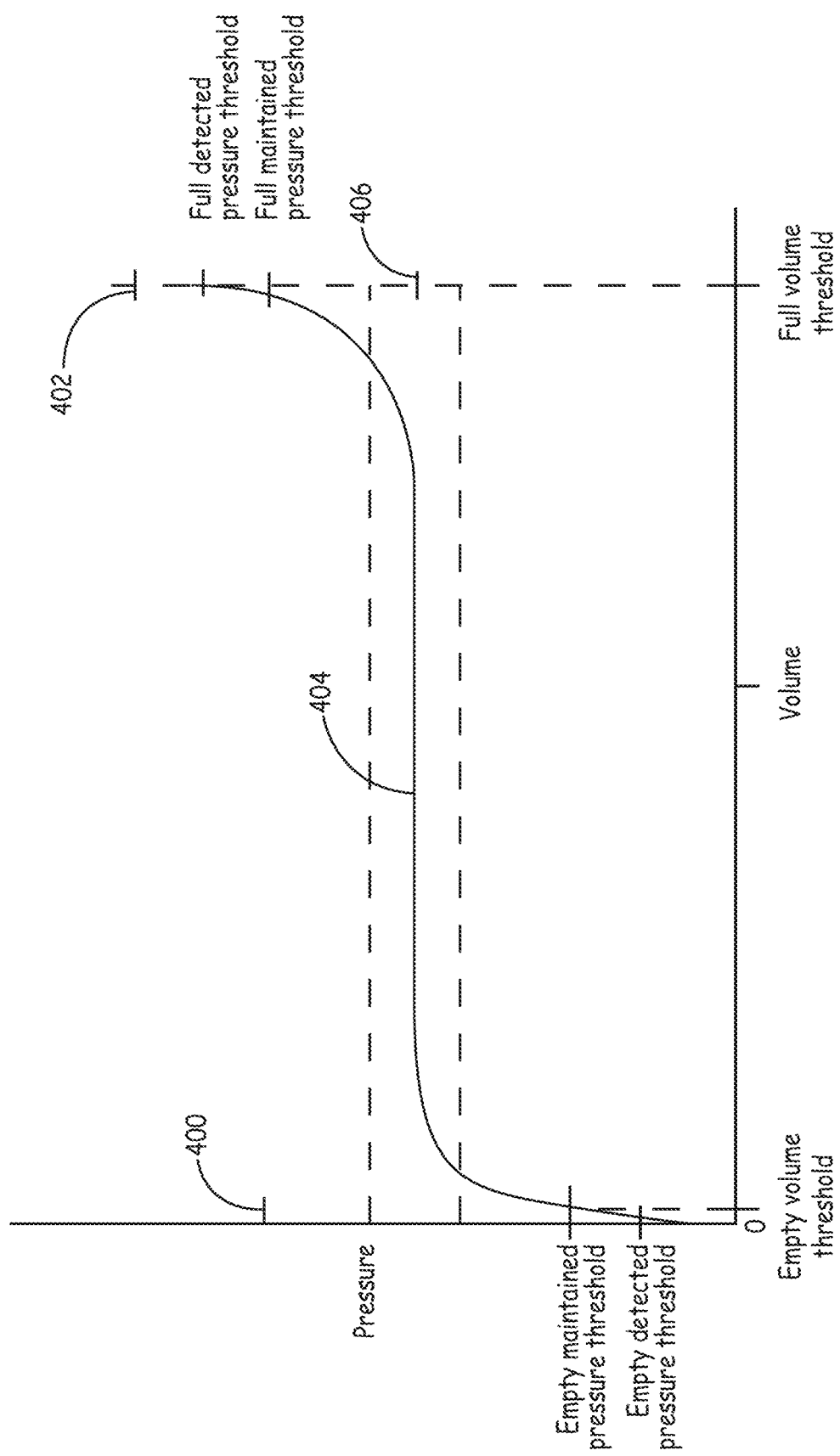
FIG. 19 is a graph showing the ideal pressure in a reservoir depending on the fill status.

FIG. 19 illustrates an ideal curve of pressure versus volume for the reservoir 32. While FIG. 19 does not illustrate the pressure that would occur during a filling or emptying operation (see FIG. 10), FIG. 19 illustrates at curve 404 what the pressure would be at various periods based upon the reservoir 32 fill status 308 if the reservoir 32 were able to maintain the ideal pressure at each fluid volume. The flat part of curve 404 shows where the reservoir 32 operates at the normal operating pressure and the propellant gases are able to compensate for the changing fluid status 308 (fluid volume) to maintain the pressure set point. Range 406 between the dashed lines, at a pressure above and below 404, illustrates an operating range that could be designated as normal or acceptable but as a departure from ideal.

Of particular note are the end points of curve 404 and when the reservoir 32 starts to report lower or higher than normal pressures. During the range indicated by 400, for example, is when the pressure in the reservoir 32 goes to a level below the ideal operating range (the point depending on the size of the reservoir 32 and other factors). Such a situation may occur when the volume of fluid in the reservoir 12 is so low that the reservoir 32 may not be able to compensate and maintain the pre-programmed pressure. At this point the pressure detected by the pressure sensor 14 reaches a point designated as the empty detected pressure threshold. The empty detected pressure threshold is that point at which the software tracking the reservoir 32 volume is able to resets the volume of fluid present in the reservoir 32, for purposes of displaying on gauge 304, to zero. The empty detected pressure threshold point on curve 404 may also be designated an empty volume threshold. In alternative embodiments the empty volume threshold and the empty detected pressure threshold may or may not be the same point on curve 404. While some small amounts of fluid may remain in the reservoir 32, the volume is at a low enough level that it can be considered zero volume for purposes of calculating the fluid status 308 for display on gauge 304. As also illustrated, at some reservoir 32 fluid volume higher than the empty detected pressure threshold, is an empty maintained pressure threshold. When the pressure goes above the empty maintained pressure threshold during refilling the calculation of the fluid status 308 begins.

The empty maintained pressure threshold may be higher than the empty detected pressure threshold because the empty detected pressure threshold may be reached during peak application of vacuum pressure during aspiration operations. However, some amount of air may leak back into reservoir 32 after aspiration that drives the detected pressure, and hence the detected volume, higher. Designating the empty maintained pressure threshold at some pressure higher than should be reached by residual air leaking into the reservoir can help to eliminate false fluid status 308 readings. Designating the detected threshold versus the maintained threshold in this manner is a known method of eliminating error in such a measurement operation. With reference to FIG. 10, the empty detected pressure threshold may be between points E and F on the graph.

A similar situation may occur when the reservoir 32 pressure is above the ideal operating range wherein the full detected pressure threshold is set at some pressure higher than the full maintained pressure threshold. A full volume threshold may likewise correspond to the point on curve 404 where the full detected pressure threshold is set.

The thresholds designated for starting the calculation of the fluid status 308 may preferably be near enough to a completely empty (or, alternatively, full) state that it provides a reliable starting point for determining the fill status 308 using the below described calculations. As may be appreciated, the full maintained pressure threshold will normally be taken into account when calculating the reservoir fill status 308 during the initial sages of a refill procedure. The amount of fluid pumped since the last time the reservoir 32 was at the full maintained pressure threshold, calculated in a manner as previously described, will be utilized to indicate the approximate fluid status 308 after the infusion device 12 has been pumping for some time. In other words, for calculating the starting point of reservoir volume when the pump is being aspirated before filling. Because the reservoir 32 may be normally fully aspirated as an initial step in a refill procedure, the empty volume threshold will then be utilized to start the calculations of fill status 308 for filling. In alternative embodiments, the reservoir 32 may be filled from a partially filled state. In still further embodiments the reservoir 32 may be rinsed one or more times before a new drug or a new concentration of the drug is placed into the reservoir, resulting in one or more full or empty states from which the software may calculate the fill status 308.

In one method, the volume added or removed from reservoir 32 may be calculated by using the starting volume of fluid in the reservoir 32 and then adding or subtracting the volume added or removed from the reservoir. The volume added or removed from the reservoir may be determined by integrating the fluid rate over time:

$$\text{Vol.\_fill} = \int_{start}^{end} \text{fluid\_rate}\, dt$$

In one embodiment the fluid rate may be determined by taking the rate of change of the pressure over time during the filling or emptying of the reservoir 32. The rate of change may be directly proportional to the fluid rate. As illustrated in FIG. 10, the slope of the graph at region D is the rate of change of the pressure over time during aspiration. Likewise, the slope at region L is illustrative of the rate of change of the pressure over time when the reservoir 32 is being filled. The software may calculate the slope in real time or near real time based upon the information transmitted to the programmer 62 through the telemetry circuit 64. The slope is then used to determine the fluid rate.

In another embodiment, the fluid rate may be determined by measuring the pressure differential between the reservoir 32 and the port 40 utilizing the pressure sensor 14. The pressure measured by the pressure sensor 14 may be positive for filling and negative for emptying, due to the insertion or extraction of fluid from the port 40, respectively. The rate of fluid being inserted into the reservoir 32 or extracted from the reservoir 32 is then calculated utilizing a known fluidic restriction constant and the formula:

Fluid Rate=Pressure Differential/Fluidic Restriction

The fluidic restriction is a known constant based upon the flow restrictions of the pump and can be measured or calculated for the pump before implantation. If the reservoir 32 starts out at an empty volume, the fill status 308 can then be calculated based on the fill rate and the known starting point. In other situations, the fill status at the start of the operation may be full or at some point between empty and full. As may be appreciated, the fill status 308 can be continually calculated as the volume in reservoir 32 goes up and down. In the present embodiment, the calculated fill status 308 can be reset to full or empty every time the reservoir 32 reaches the full volume threshold or the empty volume threshold.

Figure 20:
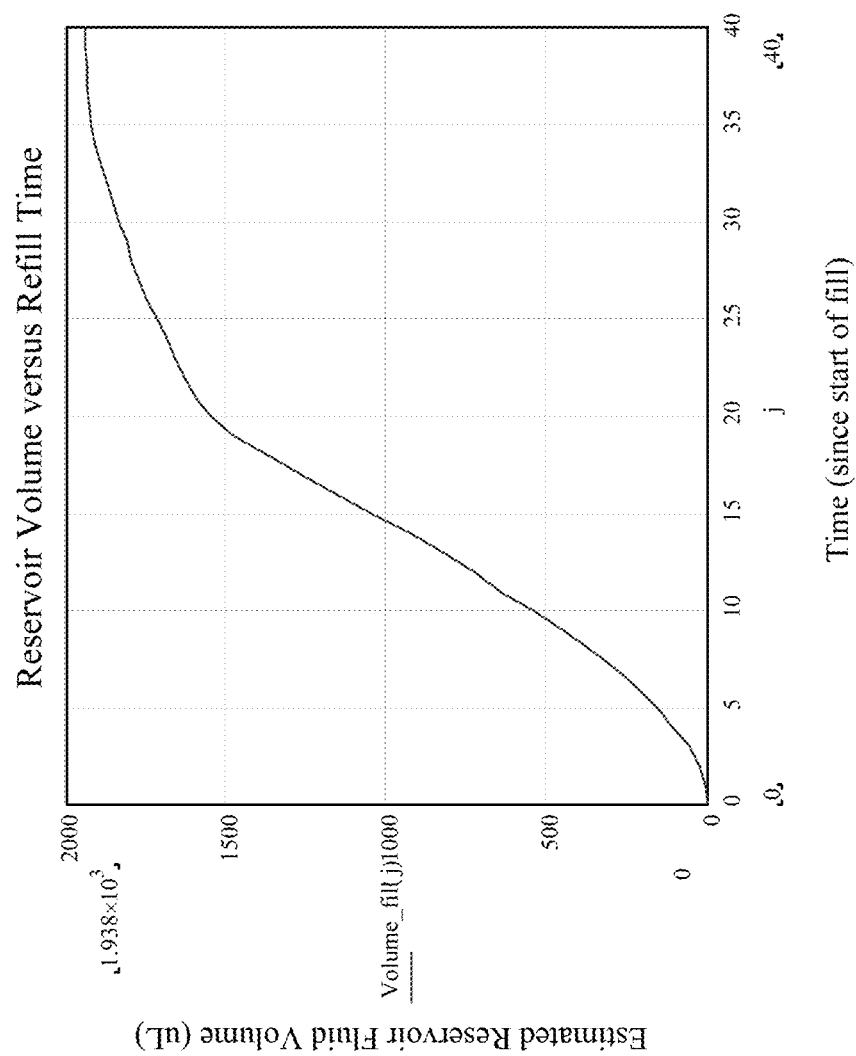
FIG. 20 is a chart showing reservoir fill status, or the estimated reservoir fluid volume, versus time during a refill operation.

FIG. 20 illustrates one example of an estimated (calculated) reservoir 32 fill status 308 over time. The fluid flow rate is integrated over the filling time to produce the fluid status displayed in the graph for a 20 mL reservoir 32. The curve illustrated in FIG. 20 roughly corresponds to the (ideal) pressure curve of FIG. 19 wherein the low fluid volume is equal to low pressure in the reservoir 32 and high fluid volume is equal to high pressure in the reservoir 32. FIG. 20 is a representative curve but may closely resemble calculated levels achieved over time that would be displayed on the gauge 304 illustrated in, for example, FIG. 11.

Figure 21:
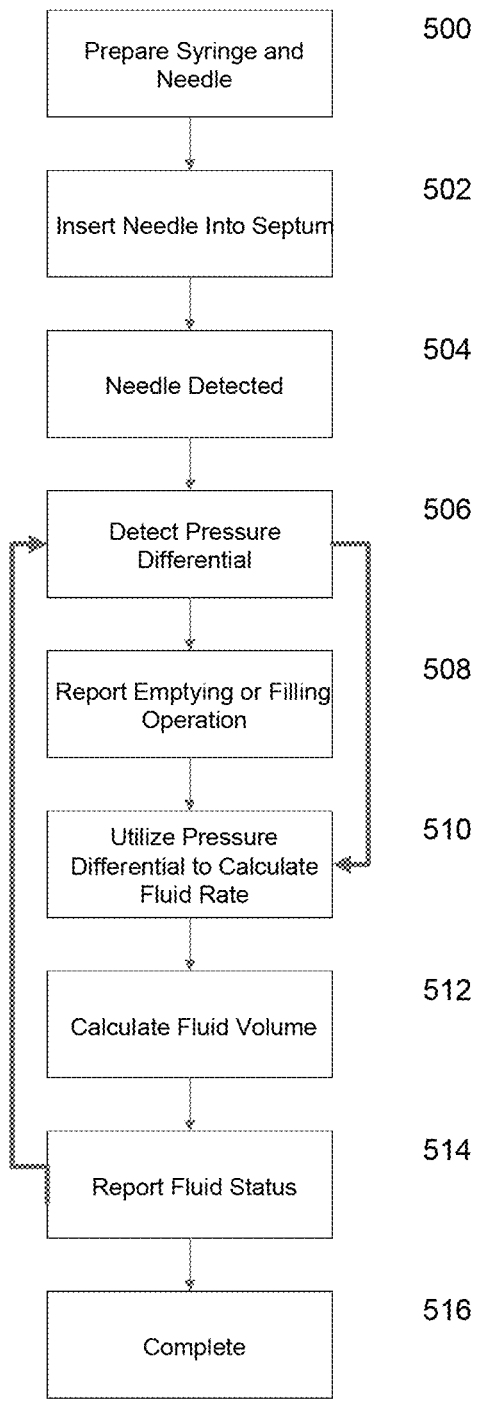
FIG. 21 is a flow diagram showing the steps of one embodiment of the present invention.

FIG. 21 illustrates a flow diagram illustrating a method of determining and displaying the fill status of the reservoir gauge. This method may be utilized with a variety of different procedures, such as inserting a needle in the catheter access port or in the fill port assembly, but is presently described for inserting the needle into the fill port assembly to inject fluid into the reservoir. The reservoir I in the empty state to start but in other embodiments may be at any level at the start. First, the refill needle and syringe are prepared (500). The needle is then inserted through the septum and into the port assembly (502). The pressure sensor detects (504) the needle and then detects fluid flow based on the pressure differential (506). The fact that a filling operation is occurring can then be reported to the user (508). The logic circuit may then utilize the pressure differential determined by pressure sensor to calculate the fluid flow rate (510) and the fluid volume/fluid status (512) based on the flow rate and the known starting fluid volume/status (in this case empty). The fluid volume/status may then be reported to the user (514). The operation of detecting the fluid pressure through reporting the fluid volume/status to the user may be repeated and the gauge updated as long as the pressure sensor continues to detect fluid flow. Once the reservoir is full or empty, or the user stops injecting fluid such that the pressure sensor no longer detects fluid flow, the operation is complete (516). In addition, if needle slips out of the fluid flow would stop and the gauge would not be updated, even if the user is still injecting fluid.

In alternative embodiments the needle and syringe may be utilized in the catheter access port, the needle may be utilized to first aspirate the reservoir, or the needle and syringe may be utilized to clean the reservoir and infusion pump. As may be appreciated, a variety of changes may be made to the method without departing from the spirit and scope of detecting fluid flow, determining a fluid state, and displaying the fluid state to the user.

One of skill in the art will understand that components or steps described herein regarding a given embodiment or set of embodiments may readily be omitted, substituted, or added from, with, or to components or steps of other embodiments or sets of embodiments, as appropriate or desirable.

What is claimed is:

1. A method for calculating a fill status of a reservoir in an implantable medical device during a procedure to refill the reservoir, the method comprising:
   determining a rate of change of the pressure as fluid is added to the reservoir via a fill port assembly in communication with the reservoir;
   determining a fluid flow rate into the reservoir based on the rate of change of the pressure;
   determining a total volume of fluid added to the reservoir by integrating the fluid flow rate over the time when fluid is added in which the pressure is sensed using the pressure sensor; and
   combining the total volume of fluid added to the reservoir with a known starting volume of fluid in the reservoir to determine a volume of fluid in the reservoir during the refill procedure.

2. The method of claim 1 wherein combining the total volume of fluid added to the reservoir with the known starting volume of fluid in the reservoir is performed by a logic circuit.

3. The method of claim 1 wherein the fluid flow rate is positive when fluid is being added to the reservoir and negative when fluid is being removed from the reservoir.

4. The method of claim 1 further comprising determining the known starting volume by subtracting a fluid volume pumped from the implantable medical device since the last time point at which the reservoir was full.

5. The method of claim 4 wherein the volume pumped from the implantable medical device is determined from multiplying the number of strokes of the pump by the volume of fluid pumped per stroke.

6. The method of claim 1 wherein the pressure sensor is in the reservoir.

7. The method of claim 1 wherein sensing the reservoir pressure further comprises:
   sensing a pressure upstream of the reservoir using the pressure sensor; and
   calculating the reservoir pressure based on a known fluidic restriction between the upstream pressure sensor and the reservoir.

8. The method of claim 1 further comprising:
   determining a rate of change of the pressure as fluid is removed from the reservoir via the fill port assembly in fluid communication with the reservoir;
   determining a fluid flow rate out of the reservoir based on the rate of change of the pressure;
   determining a total volume of fluid removed from the reservoir by integrating the fluid flow rate over the time when fluid is removed in which the pressure is sensed using the pressure sensor; and
   combining the total volume of fluid removed from the reservoir with the known starting volume of fluid in the reservoir to determine the volume of fluid in the reservoir.

9. A method for displaying a fluid status of a reservoir of an implantable medical device during a procedure to refill the reservoir, comprising:
   determining a rate of change of the pressure as fluid is added to the reservoir via a fill port assembly in communication with the reservoir;
   determining a fluid flow rate into the reservoir based on the rate of change;
   determining a total volume of fluid added to the reservoir by integrating the fluid flow rate over a time when fluid is added in which the pressure is sensed using the pressure sensor;
   combining the total volume of fluid added to the reservoir with a known starting volume of fluid in the reservoir to determine a volume of fluid in the reservoir during the refill procedure; and
   displaying the determined volume of fluid in the reservoir on a programmer.

10. The method of claim 9 further comprising updating the determined volume of fluid in the reservoir on a continuous basis.

11. The method of claim 9 wherein displaying the determined volume of fluid in the reservoir fluid status on the programmer includes displaying the determined volume of fluid in the reservoir on a gauge.

12. The method of claim 9 wherein combining the total volume of fluid added to the reservoir with the known starting volume of fluid in the reservoir is performed by a logic circuit.

13. The method of claim 9 wherein the fluid flow rate is positive when fluid is being added to the reservoir and negative when fluid is being removed from the reservoir.

14. The method of claim 9 wherein the pressure sensor is in the reservoir.

15. The method of claim 9 wherein sensing the reservoir pressure further comprises:
   sensing a pressure upstream of the reservoir using the pressure sensor; and
   calculating the reservoir pressure based on a known fluidic restriction between the upstream pressure sensor and the reservoir.

16. The method of claim 9 further comprising:
   determining a rate of change of the pressure as fluid is removed from the reservoir via the fill port assembly in communication with the reservoir;
   determining a fluid flow rate out of the reservoir based on the rate of change of the pressure;
   determining a total volume of fluid removed from the reservoir by integrating the fluid flow rate over the time when fluid is removed in which the pressure is sensed using the pressure sensor; and
   combining the total volume of fluid removed from the reservoir with the known starting volume of fluid in the reservoir to determine the volume of fluid in the reservoir.

* * * * *